United States Patent
Arase et al.

(10) Patent No.: US 9,778,257 B2
(45) Date of Patent: Oct. 3, 2017

(54) AUTOANTIBODY DETECTION METHOD, METHOD FOR TESTING POSSIBILITY OF AUTOIMMUNE DISEASE CONTRACTION, AUTOANTIBODY DETECTION REAGENT, AND AUTOIMMUNE DISEASE TEST REAGENT

(71) Applicant: OSAKA UNIVERSITY, Suita-shi, Osaka (JP)

(72) Inventors: Hisashi Arase, Osaka (JP); Kenji Tanimura, Osaka (JP); Hui Jin, Osaka (JP); Noriko Arase, Osaka (JP)

(73) Assignee: Osaka University, Osaka (JP)

( * ) Notice: Subject to any disclaimer, the term of this patent is extended or adjusted under 35 U.S.C. 154(b) by 105 days.

(21) Appl. No.: 14/905,621

(22) PCT Filed: Jan. 17, 2014

(86) PCT No.: PCT/JP2014/050796
§ 371 (c)(1),
(2) Date: Jan. 15, 2016

(87) PCT Pub. No.: WO2015/008498
PCT Pub. Date: Jan. 22, 2015

(65) Prior Publication Data
US 2017/0176432 A1    Jun. 22, 2017

(30) Foreign Application Priority Data

Jul. 17, 2013   (JP) .................................. 2013-148833

(51) Int. Cl.
*G01N 33/564*   (2006.01)
*G01N 33/569*   (2006.01)

(52) U.S. Cl.
CPC ..... *G01N 33/564* (2013.01); *G01N 33/56977* (2013.01)

(58) Field of Classification Search
None
See application file for complete search history.

(56) References Cited

U.S. PATENT DOCUMENTS

2009/0010943 A1   1/2009   Hill et al.

FOREIGN PATENT DOCUMENTS

JP    2007-52483    8/2007

OTHER PUBLICATIONS

Loizou et. al., "Measurement of anti-cardiolipin antibodies by an enzymelinked immunosorbent assay (ELISA) : standardization and quantitation of results", Clin. exp. Immunol., vol. 62, pp. 738-745 (1985).
Scott et al., "Crystal Structures of Two I-Ad-Peptide Complexes Reveal That High Affinity Can Be Achieved without Large Anchor Residues", Immunity, vol. 8, pp. 319-329 (1998).
Raychaudhuri et al., "Five amino acids in three HLA proteins explain most of the association between MHC and seropositive rheumatoid arthritis", Nat. Genet., vol. 44, pp. 291-296 (2012).
Ichikawa, et al., "β2-Glycoprotein i reactivity of monoclonal anticardiolipin antibodies from patients with the antiphospholipid syndrome", Arthritis & Rheumatism, vol. 37, Issue 10, pp. 1453-1461 (1994).
Arase, Development of Immune and Infection Control Technology Targeting Paired Receptors (Intermediate Evaluation on Research Subject) [Online], Japan Science and Technology Agency, Mar. 29, 2013—with partial translation.
Jiang et al., "Transport of misfolded endoplasmic reticulum proteins to the cell surface by MHC class II molecules", Int Immunol, vol. 25, No. 4, pp. 235-246 (2013).
Mohan et al., "A novel pathway of presentation by class II-MHC molecules involving peptides or denatured proteins important in autoimmunity", Molecular Immunology, vol. 55 (2), pp. 166-168 (2013).
International Search Report issued in International Application No. PCT/JP2014/050796, Apr. 22, 2014, 4 pages.

*Primary Examiner* — Jacob Cheu
(74) *Attorney, Agent, or Firm* — Hamre, Schumann, Mueller & Larson, P.C.

(57) ABSTRACT

The present invention provides an autoantibody detection method that can detect an autoantibody causing an autoimmune disease with high accuracy. The autoantibody detection method of the present invention includes the steps of; causing a sample and an antigen reagent comprising a denatured protein presented by an MHC class II molecule to come into contact with each other; and detecting a complex of an autoantibody in the sample and the denatured protein in the antigen reagent. By detecting a complex of the autoantibody and the denatured protein in a biological specimen isolated from a subject according to this detection method, it is possible to test the possibility of the autoimmune disease in the subject from the detection result.

11 Claims, 11 Drawing Sheets

AUTOANTIBODY DETECTION METHOD, METHOD FOR TESTING POSSIBILITY OF AUTOIMMUNE DISEASE CONTRACTION, AUTOANTIBODY DETECTION REAGENT, AND AUTOIMMUNE DISEASE TEST REAGENT

TECHNICAL FIELD

The present invention relates to an autoantibody detection method, a method for testing the possibility of an autoimmune disease, an autoantibody detection reagent, an autoimmune disease test reagent, a method for producing an autoantibody detection reagent, and a screening method for an antigen protein against an autoantibody relevant to an autoimmune disease.

BACKGROUND ART

Diagnosis of an autoimmune disease generally is done utilizing, in addition to direct determination based on the symptoms etc. of a patient, indirect determination based on the detection of an autoantibody specific to the autoimmune disease. The detection of an autoantibody usually is performed using, e.g., an ELISA method in which a purified antigen protein is immobilized on a carrier and the binding of the autoantibody with the immobilized protein is examined. However, even when patients are diagnosed with an autoimmune disease by doctors on the basis of their symptoms, the autoantibody is not necessarily detected in all the patients by the ELISA method. Thus, if diagnosis is made depending on the detection of the autoantibody by the ELISA method alone, false negative results may be obtained. Therefore, for diagnosis of an autoimmune disease, a determination method other than the autoantibody detection by the ELISA method has to be used in combination. Under these circumstances, in order to enable highly reliable diagnosis of autoimmune diseases, there are demands for a method that can detect an autoantibody with high accuracy.

CITATION LIST

Non-Patent Document(s)

[Non-Patent Document 1] S. LOIZOU et al., "Measurement of anti-cardiolipin antibodies by an enzyme-linked immunosorbent assay (ELISA) standardization and quantitation of results", Clin. exp. Immunol., Wiley, 1985, vol. 62, pp. 738-745

BRIEF SUMMARY OF THE INVENTION

Problem to be Solved by the Invention

With the foregoing in mind, it is an object of the present invention to provide an autoantibody detection method that can detect an autoantibody causing an autoimmune disease with high accuracy.

Means for Solving Problem

In order to achieve the above object, the present invention provides a detection method for detecting an autoantibody, including the steps of: causing a sample and an antigen reagent including a denatured protein presented by a major histocompatibility complex (MHC) class II molecule to come into contact with each other; and detecting a complex of an autoantibody in the sample and the denatured protein in the antigen reagent. Hereinafter, "a denatured protein presented by an MHC class II molecule" also is referred to as "a denatured protein/MHC class II".

The present invention also provides a test method for testing a possibility of an autoimmune disease, wherein a sample is a biological specimen isolated from a subject. The test method includes the steps of: detecting a complex of an autoantibody in the sample and a denatured protein presented by an MHC class II molecule by the detection method according to the present invention; and evaluating the possibility of the autoimmune disease from the result of detecting the complex in the detection step.

The present invention also provides an autoantibody detection reagent for use in the detection method according to the present invention. The autoantibody detection reagent includes: a denatured protein presented by an MHC class II molecule. The present invention also provides an autoimmune disease test reagent including the autoantibody detection reagent according to the present invention.

The present invention also provides a method for producing the autoantibody detection reagent according to the present invention. The production method includes the step of: preparing an MHC class II molecule presenting a denatured protein resulting from denaturation of a correctly folded protein by introducing a gene encoding the correctly folded protein into an MHC class II molecule expression system cell.

The present invention also provides a screening method for an antigen protein against an autoantibody relevant to an autoimmune disease, wherein a sample is a biological specimen isolated from a subject affected with an autoimmune disease. The screening method includes the steps of: detecting a complex of an autoantibody in the sample and a denatured protein presented by an MHC class II molecule by the detection method according to the present invention; and determining the denatured protein that has formed the complex with the autoantibody as an antigen protein against an autoantibody relevant to the autoimmune disease.

Effects of the Invention

It is known that, in an antigen-presenting cell, a protein antigen is degraded into peptide fragments, which are then bound to MHC class II molecules and carried to the surface of the cell, whereby the peptide fragments are presented on the surface of the cell. However, through diligent research, the inventors of the present invention made the following findings. Specifically, the inventors of the present invention first discovered that an MHC class II molecule not only presents the degraded peptide fragment, but also binds to a denatured protein resulting from misfolding in an endoplasmic reticulum (ER) and presents the denatured protein on the cell surface. The inventors of the present invention further discovered that an autoantibody recognizes and binds to the denatured protein presented on the cell surface by the MHC class II molecule. These mechanisms had not been reported at the time the present application was filed, and the inventors of the present invention first discovered these mechanisms. The inventors of the present invention conducted experiments to detect various autoantibodies using, as an antigen reagent, a purified protein used in a conventional ELISA method as described above (i.e., a correctly folded protein resulting from correct folding) or the denatured protein/MHC class II. As a result, the inventors of the present invention verified that the denatured protein/MHC class II is recognized by autoantibodies of autoimmune disease patients with higher specificity as compared with the correctly folded protein, thereby establishing the present invention. Therefore, according to the present invention in which the denatured protein/MHC class II is used as an antigen reagent for detecting an autoantibody, it is possible to detect the autoantibody involved in an autoimmune disease with high accuracy. Also, the present invention can detect autoantibodies undetectable by the ELISA method in which a correctly folded protein is used, for example. Accordingly, the present invention can inhibit the conventional problem of a false negative, thus allowing the possibility of an autoimmune disease to be determined with high accuracy. Therefore, the present invention is very useful in the fields of clinical practice and biochemistry, for example.

The reason why an autoantibody can be detected with higher accuracy by using the denatured protein/MHC class II as an antigen reagent as compared with the case where the correctly folded protein is used as an antigen reagent presumably is as follows. That is, it is presumed that an autoantibody in the sample binds to a correctly folded protein through cross-reactivity, whereas the autoantibody specifically binds to the denatured protein/MHC class II. It is to be noted, however, that this presumption does not limit the present invention by any means.

MODE FOR CARRYING OUT THE INVENTION

Autoantibody Detection Method

Figure 1:
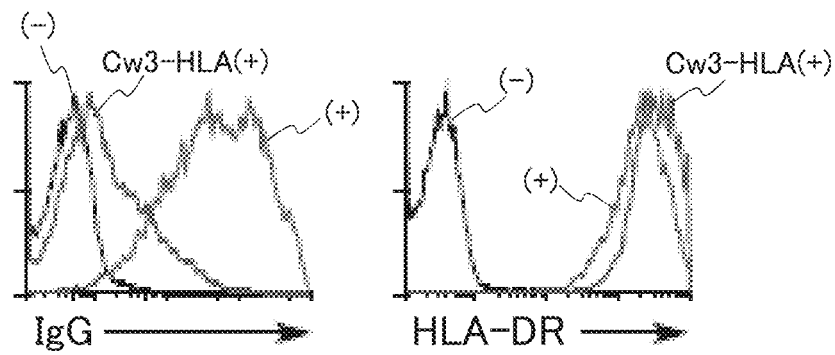
FIG. 1 shows histograms showing the expression levels of IgG and an MHC class II molecule on cell surfaces in Example 1A.

As described above, the autoantibody detection method of the present invention includes the steps of; causing a sample and an antigen reagent including a denatured protein presented by an MHC class II molecule to come into contact with each other; and detecting a complex of an autoantibody in the sample and the denatured protein in the antigen reagent.

In the detection method of the present invention, the denatured protein means a protein that is not a normal protein, for example. In the present invention, the denatured protein is, for example, a misfolded protein resulting from denaturation of folding in a correctly folded protein.

In the detection method of the present invention, the denatured protein preferably is a denatured protein presented by MHC class II molecules, obtained by introducing a gene encoding a correctly folded protein into an MHC class II molecule expression system cell. In the present invention, for example, the denatured protein preferably is a protein presented by MHC class II molecules, obtained by introducing a gene encoding a normal protein into the expression system cell, regardless of how the denatured protein is misfolded as compared with the folding in the normal protein.

Preferably, the detection method of the present invention further includes the step of preparing an MHC class II molecule presenting a denatured protein resulting from denaturation of a correctly folded protein by introducing a gene encoding the correctly folded protein into an MHC class II molecule expression system cell.

In the detection method of the present invention, the denatured protein is, for example, a protein resulting from denaturation of a correctly folded protein involved in an autoimmune disease.

In the detection method of the present invention, the denatured protein is, for example, a protein resulting from denaturation of at least one selected from the group consisting of an IgG heavy chain, thyroglobulin, β2-glycoprotein I, and a thyroid-stimulating hormone receptor.

In the detection method of the present invention, the MHC class II molecule preferably is at least one selected from the group consisting of HLA-DR, HLA-DP, and HLA-DQ. In the present invention, the MHC class II molecule is, for example, an autoimmune disease susceptible MHC class II molecule.

In the detection method of the present invention, the MHC class II molecules include HLA-DR, and the denatured protein is a denatured protein resulting from denaturation of an IgG heavy chain, for example. With this configuration, for example, an autoantibody relevant to rheumatoid arthritis can be detected.

In the present invention, for example, the MHC class II molecules include HLA-DR, and the denatured protein is a denatured protein resulting from denaturation of thyroglobulin, for example. With this configuration, for example, an autoantibody relevant to Hashimoto's disease can be detected.

In the present invention, the MHC class II molecules include HLA-DR, and the denatured protein is a denatured protein resulting from denaturation of β2-glycoprotein I, for example. With this configuration, for example, an autoantibody relevant to anti-phospholipid antibody syndrome can be detected.

In the present invention, the MHC class II molecules include HLA-DP, and the denatured protein is a denatured protein resulting from denaturation of a thyroid-stimulating hormone receptor, for example. With this configuration, for example, an autoantibody relevant to Basedow's disease (Graves' disease) can be detected.

The autoantibody detection method according to the present invention is characterized in that, in the detection step, a complex of "an autoantibody" in the sample and "a denatured protein presented by an MHC class II molecule (denatured protein/MHC class II)" in the antigen reagent is caused to be formed and then the complex is detected. Other steps and conditions are not particularly limited.

In the present invention, the term "autoantibody" means, for example, an antibody produced in a subject from which the sample is derived and is directed against a self-component (autoantigen) of the subject. Specific examples of the autoantibody include an antibody produced in an animal individual against an autoantigen of the individual. The autoantibody is relevant to an autoimmune disease as described above, and it is known that determination of the presence or absence of the autoantibody or the amount of the autoantibody is important in diagnosis, treatment, or prognosis determination of the autoimmune disease. Therefore, the autoantibody detection method of the present invention is very useful in diagnosis etc. of autoimmune diseases, for example.

(1) Antigen Reagent

In the present invention, an antigen reagent for detecting an autoantibody also can be referred to as an autoantibody detection reagent. The antigen reagent is, as described above, a denatured protein presented by an MHC class II molecule. The form of the denatured protein is not particularly limited. As an example, the antigen reagent may be in the form of a complex of the denatured protein and the MHC class II molecule, in which the denatured protein is bound to the binding groove of the MHC class II molecule. The complex may be in the form of the complex alone, or in the form of a cell presenting the complex on the surface thereof (e.g., an antigen-presenting cell), for example. As another example, the antigen reagent may be in the form of the denatured protein that is in the state where the binding with the MHC class II molecule has been dissociated (the denatured protein not bound to the MHC class II molecule), for example.

In the present invention, the denatured protein is a protein resulting from denaturation of folding in a correctly folded protein, for example. The correctly folded protein means a protein resulting from correct folding, for example.

(2) Preparation of Antigen Reagent

In the present invention, the denatured protein preferably is a denatured protein presented by an MHC class II molecule, obtained by introducing a gene encoding a correctly folded protein into an MHC class II molecule expression system cell, for example. Thus, for example, the present invention may include, prior to the contact step, the step of preparing the denatured protein/MHC class II, i.e., the step of preparing an MHC class II molecule presenting a denatured protein resulting from denaturation of a correctly folded protein by introducing a gene encoding the correctly folded protein into an MHC class II molecule expression system cell.

If a gene encoding a correctly folded protein is introduced to the MHC class II molecule expression system cell, misfolding is caused in a protein expressed by the gene in the expression system cell, instead of correct folding as in a correctly folded protein, as described above. Then, the denatured protein resulting from this misfolding binds to the expressed MHC class II molecule and is presented on the surface of the cell.

The correctly folded protein is, for example, a protein involved in an autoimmune disease, and specific examples thereof include proteins known to bind to autoantibodies in autoimmune diseases. As described above, detection of an autoantibody has been performed by synthesizing a protein conventionally considered as an autoantigen in an autoimmune disease, immobilizing the purified protein to a carrier as an antigen protein, and detecting the formation of a complex resulting from the binding of the antigen protein and the autoantibody. However, even if a protein is generated from the same base sequence, the correlation between an autoimmune disease and the result of detecting an autoantibody is higher in the case where the detection result is the result of detecting an autoantibody that binds to a denatured protein resulting from misfolding presented by the MHC class II molecules, as compared with the case where the detection result is the result of detecting an autoantibody that binds to a correctly folded protein as in the conventional art, as described above. Therefore, in the present invention, it is preferable that, for example, a gene encoding a correctly folded protein conventionally known to bind to an autoantibody is introduced to an MHC class II molecule expression system cell, thereby causing a protein expressed by the coding gene to be presented by MHC class II molecules as a denatured protein resulting from misfolding, and the thus-obtained denatured protein is used as an antigen reagent.

The correctly folded protein is not particularly limited, and may be a known protein, for example. The source of the correctly folded protein is not particularly limited, and examples thereof include humans and non-human animals excluding humans. Examples of the non-human animals include mice, rats, dogs, monkeys, rabbits, sheep, and horses.

The correctly folded protein is a protein involved in an autoimmune disease as described above, and specific examples thereof include proteins known to bind to autoantibodies. The correctly folded protein is not particularly limited, and examples thereof include those shown in Table 1 below, such as an IgG heavy chain, thyroglobulin, β2-glycoprotein I (β2-GPI), insulin, thyroid peroxidase, and a thyroid-stimulating hormone receptor (TSHR). In the present invention, the denatured protein is, for example, a denatured protein resulting from misfolding as compared with correct folding in each of these correctly folded proteins. In the present invention, specific examples are as follows: a denatured protein resulting from denaturation of an IgG heavy chain serves as an antigen reagent against an autoantibody relevant to, e.g., rheumatoid arthritis; a denatured protein resulting from denaturation of thyroglobulin serves as an antigen reagent against an autoantibody relevant to, e.g., Hashimoto's disease; a denatured protein resulting from denaturation of β2-glycoprotein I serves as an antigen reagent against an autoantibody relevant to anti-phospholipid antibody syndrome; and a denatured protein resulting from denaturation of TSHR serves as an antigen reagent against an autoantibody relevant to Basedow's disease.

The source of the MHC class II molecule is not particularly limited, and examples thereof include humans and non-human animals (animals excluding humans). Examples of the non-human animals include mice, rats, dogs, monkeys, rabbits, sheep, and horses. The source of the MHC class II molecule may be the same as or different from the source of the normal protein, for example.

The MHC class II molecule is a complex of an α-chain and a β-chain. The types of the α-chain and the β-chain are not particularly limited, and the haplotypes of the genes encoding the α-chain and the β-chain are not particularly limited.

When the MHC class II molecule is derived from a human, the α-chain of the MHC class II molecule is, for example, an α-chain of the MHC class II molecule encoded by an HLA-DPA gene locus, an HLA-DQA gene locus, or an HLA-DRA gene locus, and the β-chain of the MHC class II molecule is, for example, a β-chain of the MHC class II molecule encoded by an HLA-DPB gene locus, an HLA-DQB gene locus, or an HLA-DRB gene locus. The haplotypes of the MHC class α-chain and β-chain at the respective gene loci are not particularly limited. The MHC class II molecule is, for example, a molecule including either one of the α-chain and the β-chain, and preferably is a molecule including both the α-chain and the β-chain.

The MHC class II molecule preferably is HLA-DR, HLA-DP, HLA-DQ, or the like. In particular, examples of the MHC class II molecule include MHC class II molecules relevant to autoimmune diseases listed in Table 1 below.

Examples of the HLA-DR include HLA-DR1, HLA-DR2, HLA-DR3, HLA-DR4, HLA-DR5, HLA-DR6, HLA-DR7, HLA-DR8, HLA-DR9, HLA-DR10, HLA-DR11, HLA-DR12, HLA-DR13, HLA-DR14, HLA-DR15, HLA-DR52, and HLA-DR53. The HLA-DR may be, for example, a molecule including: HLA-DRA such as HLA-DRA1 as the α-chain; and HLA-DRB such as HLA-DRB1, HLA-DRB3, HLA-DRB4, or HLA-DRB5 as the β-chain. Specific examples of the α-chain include alleles such as HLA-DRA1*01, and specific examples of the β-chain include alleles such as HLA-DRB1*01, HLA-DRB1*03, HLA-DRB1*04, HLA-DRB1*07, HLA-DRB1*08, HLA-DRB1*09, HLA-DRB1*10, HLA-DRB1*11, HLA-DRB1*12, HLA-DRB1*13, HLA-DRB1*14, HLA-DRB1*15, HLA-DRB1*16, HLA-DRB3*01, HLA-DRB4*01, and HLA-DRB5*01.

Examples of the HLA-DQ include HLA-DQ1, HLA-DQ2, HLA-DQ3, E0HLA-DQ4, HLA-DQ5, HLA-DQ6, HLA-DQ7, and HLA-DQ8. The HLA-DQ may be, for example, a molecule including: HLA-DQA such as HLA-DQA1 as the α-chain; and HLA-DQB such as HLA-DQB1 as the β-chain. Specific examples of the α-chain include alleles such as HLA-DQA1*01, HLA-DQA1*02, HLA-DQA1*03, HLA-DQA1*04, HLA-DQA1*05, and HLA-DQA1*06, and specific examples of the β-chain include alleles such as HLA-DQB1*02, HLA-DQB1*03, HLA-DQB1*04, HLA-DQB1*05, and HLA-DQB1*06.

Examples of the HLA-DP include HLA-DP1, HLA-DP2, HLA-DP3, HLA-DP4, and HLA-DP5. The HLA-DP may be, for example, a molecule including: HLA-DPA such as HLA-DPA1 as the α-chain; and HLA-DPB such as HLA-DPB1 as the β-chain. Specific examples of the α-chain include alleles such as HLA-DPA1*01, HLA-DPA1*02, HLA-DPA1*03, and HLA-DPA1*04, and specific examples of the β-chain include alleles such as HLA-DPB1*02, HLA-DPB1*04, HLA-DPB1*05, and HLA-DPB1*09.

Each of the above-described alleles is not particularly limited, and may be as shown in Table 1 below, for example.

The MHC class II molecule may be, for example, an autoimmune disease susceptible MHC class II molecule, as described above. The autoimmune disease susceptible MHC class II molecule is, for example, an MHC class II molecule including at least one of MHC class α-chain and β-chain with relatively high probability to develop the autoimmune disease as compared with other haplotypes (alleles) of MHC class α-chains and β-chains. One kind of MHC class II molecule may be used, or two or more kinds of MHC class II molecules may be used in combination, for example.

In the denatured protein/MHC class II, the combination of the MHC class II molecule and the denatured protein is not particularly limited. Specific examples of the combination include those shown in Tables 1A to 1L below, in which the combinations of the MHC class II molecule and the denatured protein are shown in relation to the autoimmune diseases. One of the combinations may be used, or two or more of the combinations may be used in combination, for example.

TABLE 1A

| Autoimmune disease | MHC class II molecule | Denatured protein |
|---|---|---|
| Rheumatoid arthritis | HLA-DRB1*04 allele (DR4) | IgG heavy chain |
| | HLA-DRB1*04:01 | type II collagen |
| | HLA-DRB1*04:02 | fibrinogen |
| | HLA-DRB1*04:03 | α-enolase |
| | HLA-DRB1*04:04 | vimentin |
| | HLA-DRB1*04:05 | Bip |
| | HLA-DRB1*04:06 | glucose-6-phosphate |

TABLE 1A-continued

| Autoimmune disease | MHC class II molecule | Denatured protein |
|---|---|---|
| | HLA-DRB1*04:07 | isomerase |
| | HLA-DRB1*04:08 | |
| | HLA-DRB1*04:09 | |
| | HLA-DRB1*04:10 | |
| | HLA-DRB1*04:11 | |
| | HLA-DRB1*04:12 | |
| | HLA-DRB1*04:13 | |
| Hashimoto's disease | HLA-DRB4*01 allele HLA-DRB4*01:03 (HLA-DR53) | thyroglobulin thyroid peroxidase |
| Anti-phospholipid antibody syndrome | HLA-DRB1*04 allele HLA-DRB1*04:02 HLA-DRB1*07 allele HLA-DRB1*07:01 | β2 glycoprotein I prothrombin |
| Narcolepsy | HLA-DQB1*06 allele HLA-DQB1*06:02 | orexin |
| Insulin autoimmune syndrome | HLA-DRB1*04 allele HLA-DRB1*04:06 | insulin |
| Buerger's disease | HLA-DRB1*04 allele HLA-DRB1*04:05 HLA-DQB1*04:01 HLA-DQA1*03 allele HLA-DPB1*05 allele HLA-DPB1*05:01 HLA-DRB1*16 allele HLA-DRB1*16:02 | Scl-70 β2 glycoprotein myeloperoxidase proteinase 3 |

TABLE 1B

| Autoimmune disease | MHC class II molecule | Denatured protein |
|---|---|---|
| Type I diabetes | HLA-DRB1*04 allele HLA-DRB1*04:01 HLA-DRB1*03 allele HLA-DRB1*03:01 HLA-DQA1*05 allele HLA-DQA1*05:01 HLA-DQB1*02 allele HLA-DQB1*02:01 HLA-DQA1*03 allele HLA-DQA1*03:01 HLA-DQB1*03:02 | insulin glutamate decarboxylase (GAD) (GAD65) carboxypeptidase H tyrosine phosphatase-like protein insulinoma antigen-2 (IA-2) IA-2b (phogrin, ICA512) Imogen-38 Islet-specific glucose-6-phosphatase catalytic subunit-related protein (IGRP) |
| Multiple sclerosis | HLA-DRB1*15 allele (DR15) HLA-DRB1*15:01 HLA-DRB1*15:02 HLA-DRB1*15:03 HLA-DRB1*15:04 HLA-DRB1*15:05 HLA-DRB1*15:07 HLA-DQB1*06 allele (DQ6) HLA-DQB1*06:01 HLA-DQB1*06:02 HLA-DQB1*06:03 HLA-DQB1*06:04 HLA-DQB1*06:05 HLA-DQB1*06:09 | β2 glycoprotein myeloperoxidase myelin basic protein proteolipid protein myelin-associated oligodendrocyte basic glycoprotein oligodendrocyte-specific protein |
| Neuromyelitis optica | HLA-DPB1*05 allele HLA-DPB1*05:01 | AQP4 |
| Basedow's disease (Graves' disease) | HLA-DPB1*05 allele HLA-DPB1*05:01 | TSH receptor (thyroid-stimulating hormone receptor, TSHR) |

TABLE 1C

| Autoimmune disease | MHC class II molecule | Denatured protein |
|---|---|---|
| Primary biliary cirrhosis | HLA-DRB1*16 allele HLA-DRB1*16:02 | glycoprotein 210 p62 sp100 sulfite oxidase sarcosine dehydrogenase glycogen phosphorylase transglutaminase |
| Systemic lupus erythematosus | HLA-DRB1*15 allele HLA-DRB1*15:01 HLA-DRB1*15 allele (DR2) HLA-DRB1*15:01 HLA-DRB1*15:02 HLA-DRB1*15:03 HLA-DRB1*16 allele (DR2) HLA-DRB1*16:01 HLA-DRB1*16:02 HLA-DRB1*03 allele (DR3) HLA-DRB1*03:01 HLA-DRB1*03:02 HLA-DRB1*03:03 HLA-DRB1*03:04 HLA-DRB1*03:07 | NKG2A β2 glycoprotein U1-RNP U2-RNP U4/6-RNP U5-RNP |
| Crohn's disease | HLA-DRB1*04 allele HLA-DRB1*04:05 HLA-DRB1*15 allele HLA-DRB1*15:02 | glycoprotein 2 CUZD1 GM-CSF |
| Ulcerative colitis | HLA-DPB1*09 allele HLA-DPB1*09:01 | glycoprotein 2 type VII collagen GM-CSF proteinase 3 |
| Mixed connective-tissue disease | HLA-DPB1*04 allele HLA-DPB1*04:01 | nuclear ribonucleoprotein (U1-RNP) |
| Goodpasture's syndrome | HLA-DRB1*15 allele (DR15) HLA-DRB1*15:01 HLA-DRB1*15:02 HLA-DRB1*15:03 HLA-DRB1*15:04 HLA-DRB1*15:05 HLA-DRB1*15:07 | type IV collagen α3 |

TABLE 1D

| Autoimmune disease | MHC class II molecule | Denatured protein |
|---|---|---|
| Membranous nephropathy | HLA-DRB1*15 allele (DR2) HLA-DRB1*15:01 HLA-DRB1*15:02 HLA-DRB1*15:03 HLA-DRB1*16 allele (DR2) HLA-DRB1*16:01 HLA-DRB1*16:02 HLA-DRB1*03 allele (DR3) HLA-DRB1*03:01 HLA-DRB1*03:02 HLA-DRB1*03:03 HLA-DRB1*03:04 HLA-DRB1*03:07 | phospholipase A2 receptor |
| Sjogren's syndrome | HLA-DRB1*03 allele (DR3) HLA-DRB1*03:01 HLA-DRB1*03:02 HLA-DRB1*03:03 HLA-DRB1*03:04 HLA-DRB1*03:07 | TRIM21 (Ro52) Ro60 |
| Wegener's granulomatosis | HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 | myeloperoxidase proteinase 3 |

TABLE 1D-continued

| Autoimmune disease | MHC class II molecule | Denatured protein |
|---|---|---|
| | HLA-DRB1*04:07 | |
| | HLA-DRB1*04:08 | |
| | HLA-DRB1*04:09 | |
| | HLA-DRB1*04:10 | |
| | HLA-DRB1*04:11 | |
| | HLA-DRB1*04:12 | |
| | HLA-DRB1*04:13 | |
| | HLA-DRB1*13 allele (DR13) | |
| | HLA-DRB1*13:01 | |
| | HLA-DRB1*13:02 | |
| | HLA-DRB1*13:03 | |
| | HLA-DRB1*13:04 | |
| | HLA-DRB1*13:05 | |
| | HLA-DRB1*13:06 | |
| | HLA-DRB1*13:07 | |
| | HLA-DRB1*13:08 | |
| | HLA-DRB1*13:10 | |
| | HLA-DRB1*15 allele (DR15) | |
| | HLA-DRB1*15:01 | |
| | HLA-DRB1*15:02 | |
| | HLA-DRB1*15:03 | |
| | HLA-DRB1*15:04 | |
| | HLA-DRB1*15:05 | |
| | HLA-DRB1*15:07 | |

TABLE 1E

| Autoimmune disease | MHC class II molecule | Denatured protein |
|---|---|---|
| Dilated cardio-myopathy | HLA-DRB1*01 allele (DR1) HLA-DRB1*01:01 HLA-DRB1*01:02 HLA-DRB1*01:03 HLA-DRB1*01:05 HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 HLA-DRB1*04:07 HLA-DRB1*04:08 HLA-DRB1*04:09 HLA-DRB1*04:10 HLA-DRB1*04:11 HLA-DRB1*04:12 HLA-DRB1*04:13 HLA-DRB1*11 allele (DR5) HLA-DRB1*11:01 HLA-DRB1*11:02 HLA-DRB1*11:03 HLA-DRB1*11:04 HLA-DRB1*11:06 HLA-DRB1*11:09 HLA-DRB1*12 allele (DR5) HLA-DRB1*12:01 | β1-adrenoceptor M2 muscarinic receptor |

TABLE 1F

| Autoimmune disease | MHC class II molecule | Denatured protein |
|---|---|---|
| Pemphigus | HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 HLA-DRB1*04:07 HLA-DRB1*04:08 HLA-DRB1*04:09 HLA-DRB1*04:10 HLA-DRB1*04:11 HLA-DRB1*04:12 HLA-DRB1*04:13 HLA-DRB1*08 allele (DR8) HLA-DRB1*08:01 HLA-DRB1*08:02 HLA-DRB1*08:03 HLA-DRB1*08:04 HLA-DRB1*08:05 HLA-DRB1*08:06 HLA-DRB1*14 allele (DR14) HLA-DRB1*14:01 HLA-DRB1*14:02 HLA-DRB1*14:03 HLA-DRB1*14:04 HLA-DRB1*14:05 HLA-DRB1*14:06 HLA-DRB1*14:07 HLA-DRB1*14:08 HLA-DRB1*14:10 | desmoglein 1 desmoglein 3 |

TABLE 1F-continued

| Autoimmune disease | MHC class II molecule | Denatured protein |
|---|---|---|
| Bullous pemphigoid | HLA-DQB1*03 allele HLA-DQB1*03:01 | collagen 17 |

TABLE 1G

| Autoimmune disease | MHC class II molecule | Denatured protein |
|---|---|---|
| Vilitigo vulgaris | HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 HLA-DRB1*04:07 HLA-DRB1*04:08 HLA-DRB1*04:09 HLA-DRB1*04:10 HLA-DRB1*04:11 HLA-DRB1*04:12 HLA-DRB1*04:13 HLA-DRB1*13 allele (DR6) HLA-DRB1*13:01 HLA-DRB1*13:02 HLA-DRB1*13:03 HLA-DRB1*13:05 HLA-DRB1*13:08 HLA-DRB1*14 allele (DR6) HLA-DRB1*14:01 HLA-DRB1*14:02 HLA-DRB1*14:03 HLA-DRB1*14:04 HLA-DRB1*14:05 HLA-DRB1*14:06 HLA-DQB1*03 allele (DQ3) HLA-DQB1*03:01 HLA-DQB1*03:02 HLA-DQB1*03:03 HLA-DQB1*03:04 HLA-DQB1*03:05 HLA-DRB1*14 allele (DR14) HLA-DRB1*14:01 HLA-DRB1*14:02 HLA-DRB1*14:03 HLA-DRB1*14:04 HLA-DRB1*14:05 HLA-DRB1*14:06 HLA-DRB1*14:07 HLA-DRB1*14:08 HLA-DRB1*14:10 | tyrosinase TRP-1 TRP-2 |

TABLE 1H

| Autoimmune disease | MHC class II molecule | Denatured protein |
|---|---|---|
| Scleroderma | HLA-DRB1*11 allele HLA-DRB1*11:04 HLA-DQB1*03 allele HLA-DRB5*01 allele HLA-DRB5*01:05 HLA-DRB1*15 allele HLA-DRB1*15:02 HLA-DQB1*06 allele HLA-DQB1*06:01 HLA-DRB1*08 allele HLA-DRB1*08:02 | topoisomerase I RNA polymerase fibrillarin Th-To U1RNP |
| Multiple myositis/ dermatitis | HLA-DRB1*01 allele HLA-DRB1*01:01 HLA-DRB1*04 allele HLA-DRB1*04:05 HLA-DRB1*03 allele HLA-DQA1*05 allele | histidine-tRNA ligase (Jo1) soluble nuclear antigen PM-1 TIF1γ CADM-140 |
| Myasthenia gravis | HLA-DRB1*03 allele (DR3) HLA-DRB1*03:01 HLA-DRB1*03:02 HLA-DRB1*03:03 HLA-DRB1*03:04 HLA-DRB1*03:07 HLA-DRB1*15 allele (DR2) HLA-DRB1*15:01 HLA-DRB1*15:02 HLA-DRB1*15:03 HLA-DRB1*16 allele (DR2) HLA-DRB1*16:01 HLA-DRB1*16:02 HLA-DRB1*15 allele HLA-DRB1*15:01 | acetylcholine receptor |

TABLE 1H-continued

| Autoimmune disease | MHC class II molecule | Denatured protein |
|---|---|---|
| | HLA-DQB1*03 allele | |
| | HLA-DPB1*02 allele | |
| | HLA-DPB1*02:01 | |

TABLE 1I

| Autoimmune disease | MHC class II molecule | Denatured protein |
|---|---|---|
| Idiopathic thrombocytopenic purpura (ITP) | HLA-DRB1*11 allele HLA-DRB1*04 allele HLA-DRB1*04:10 HLA-DRB1*09 allele HLA-DRB1*09:01 | glycoprotein II b glycoprotein III a |
| Idiopathic Addison's disease | HLA-DRB1*03 allele HLA-DRB1*03:01 HLA-DRB1*04 allele HLA-DRB1*04:04 | 21-hydroxylase (P450c21) |
| Idiopathic autoimmune hepatitis | HLA-DRB1*03 allele HLA-DRB1*03:01 HLA-DRB3*01 allele HLA-DRB3*01:01 HLA-DRB1*04 allele HLA-DRB1*04:01 HLA-DRB1*07 allele | cytochrome P450db1 liver cytokeratin 8, 18 glutathione-S-transferase (GST) |
| Harada disease | HLA-DRB1*04 allele HLA-DRB1*04:05 | tyrosinase-related protein (TRP) 1 TRP2 |
| ANCA-associated vasculitis | HLA-DRB1*09 allele HLA-DRB1*09:01 HLA-DRB1*04 allele HLA-DRB1*04:05 | myeloperoxidase proteinase 3 |
| Autoimmune pancreatitis | HLA-DRB1*04 allele HLA-DRB1*04:05 HLA-DQB1*04:01 | amylase-2α HSP-10 plasminogen-binding protein pancreatic secretory trypsin inhibitor |
| Atrophic gastritis | HLA-DQA1*01 allele HLA-DQA1*01:02 | proton pump |

TABLE 1J

| Autoimmune disease | MHC class II molecule | Denatured protein |
|---|---|---|
| Primary sclerosing cholangitis | HLA-DRB1*03 allele HLA-DQA1*05 allele HLA-DQA1*05:01 HLA-DQB1*02 allele | proteinase 3 E2 subunits of 2-oxoacid dehydrogenase complexes Sp-100/PML/SUMO gp-210/NUP62 |
| Aortitis syndrome (Takayasu's arteritis) | HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 HLA-DRB1*04:07 HLA-DRB1*04:08 HLA-DRB1*04:09 HLA-DRB1*04:10 HLA-DRB1*04:11 HLA-DRB1*04:12 HLA-DRB1*04:13 | hHSP60 β2 glycoprotein I annexin V |
| Autoimmune hemolytic anemia | HLA-DQB1*06 allele (DQ6) HLA-DQB1*06:01 HLA-DQB1*06:02 HLA-DQB1*06:03 HLA-DQB1*06:04 HLA-DQB1*06:05 HLA-DQB1*06:09 | molecules expressed on erythrocytes |
| Autoimmune inner ear disorder | HLA-DRB1*03 allele HLA-DRB1*03:01 HLA-DRB3*01 allele HLA-DRB3*01:01 HLA-DQB1*02 allele HLA-DQB1*02:01 HLA-DPB1*04 allele HLA-DPB1*04:01 | molecules expressed in the inner ear |
| Idiopathic azoospermi | HLA-DRB1*13 allele HLA-DRB1*13:02 HLA-DQB1*06 allele HLA-DQB1*06:04 | follicle-stimulating hormone molecules expressed in sperms |
| Acute disseminated encephalomyelitis | HLA-DRB1*15 allele HLA-DRB1*15:01 HLA-DRB1*15:03 HLA-DQB1*06 allele HLA-DQB1*06:02 | myelin oligodendrocyte glycoprotein |

TABLE 1K

| Autoimmune disease | MHC class II molecule | Denatured protein |
|---|---|---|
| Alopecia areata | HLA-DRB1*11 allele HLA-DRB1*11:04 HLA-DQB1*03 allele HLA-DQB1*03:01 | tyrosinase gp100 lamin A MCHR1 tyrosine hydroxylase |
| Autoimmune cardiomyopathy | HLA-DQB1*03 allele (DQ8) HLA-DQB1*03:02 HLA-DQB1*03:04 HLA-DQB1*03:05 | laminin |
| Chronic inflammatory demyelinating polyradiculo-neuropathy | HLA-DRB1*15 allele (DR2) HLA-DRB1*15:01 HLA-DRB1*15:02 HLA-DRB1*15:03 HLA-DRB1*16 allele (DR2) HLA-DRB1*16:01 HLA-DRB1*16:02 | contactin-1 |
| Churg-Strauss syndrome | HLA-DRB1*04 allele | molecules expressed in neutrophils |
| Idiopathic pulmonary fibrosis | HLA-DRB1*15 allele HLA-DRB1*15:01 | topoisomerase II |
| Guillain-Barre syndrome | HLA-DQB1*03 allele | gangliosides sulfatide cardiolipin |
| Lichen sclerosus | HLA-DRB1*12 allele | molecules expressed in circulating basement membrane zone |
| Microscopic polyangiitis | HLA-DRB1*09 allele HLA-DRB1*09:01 HLA-DQB1*03 allele HLA-DQB1*03:03 | proteinase 3 |
| Paroxysmal nocturnal hemoglobinuria | HLA-DRB1*15 allele (DR2) HLA-DRB1*15:01 HLA-DRB1*15:02 HLA-DRB1*15:03 HLA-DRB1*16 allele (DR2) HLA-DRB1*16:01 HLA-DRB1*16:02 | diazepam-binding inhibitor-related protein 1 |

TABLE 1L

| Autoimmune disease | MHC class II molecule | Denatured protein |
|---|---|---|
| Relapsing polychondritis | HLA-DRB1*04 allele (DR4) HLA-DRB1*04:01 HLA-DRB1*04:02 HLA-DRB1*04:03 HLA-DRB1*04:04 HLA-DRB1*04:05 HLA-DRB1*04:06 HLA-DRB1*04:07 HLA-DRB1*04:08 HLA-DRB1*04:09 HLA-DRB1*04:10 HLA-DRB1*04:11 HLA-DRB1*04:12 HLA-DRB1*04:13 | type II collagen |
| Sarcoidosis | HLA-DRB1*11 allele HLA-DRB1*11:01 | molecules expressed in endothelial cells |
| Stiff person syndrome | HLA-DQB1*02 allele HLA-DQB1*02:01 | amphiphysin |

Specific examples are as follows. For example, when the MHC class II molecules include HLA-DR and the denatured protein is a denatured protein resulting from denaturation of an IgG heavy chain, an autoantibody relevant to rheumatoid arthritis can be detected. The HLA-DR may be, for example, a molecule including HLA-DRA1*01 as the α-chain and at least one selected from the group consisting of HLA-DRB1*01, HLA-DRB1*03, HLA-DRB1*04, and HLA-DRB1*15 as the β-chain. For example, when the MHC class II molecules include HLA-DR and the denatured protein is a denatured protein resulting from denaturation of thyroglobulin, an autoantibody relevant to Hashimoto's disease can be detected. The HLA-DR may be, for example, a molecule including HLA-DRA1*01 as the α-chain and at least one selected from the group consisting of HLA-DRB1*01, HLA-DRB1*04, HLA-DRB1*14, HLA-DRB1*15, and HLA-DRB4*01 as the β-chain. For example, when the MHC class II molecules include HLA-DR and the denatured protein is a denatured protein resulting from denaturation of β2-glycoprotein I, an autoantibody relevant to anti-phospholipid antibody syndrome can be detected. The HLA-DR may be, for example, a molecule including HLA-DRA1*01 as the α-chain and at least one of HLA-DRB1*04 and HLA-DRB1*07 as the β-chain. For example, when the MHC class II molecules include HLA-DP and the denatured protein is a denatured protein resulting from denaturation of TSHR, an autoantibody relevant to Basedow's disease can be detected. The HLA-DP may be, for example, a molecule including HLA-DPA1*02 as the α-chain and HLA-DPB1*05 as the β-chain.

The MHC class II molecule expression system cell is not particularly limited as long as, for example, it is a cell that expresses the MHC class II molecule and can express the gene encoding a correctly folded protein introduced thereto. The cell may have a gene encoding the MHC class II molecule either as an endogenous gene or an extraneous gene. In the former case, the gene encoding a correctly folded protein may be introduced to a host cell having a gene encoding the MHC class II molecule as an endogenous gene, for example. In the latter case, the gene encoding a correctly folded protein and a gene encoding the MHC class II molecule may together be introduced to a host cell, for example.

The gene encoding a correctly folded protein may be, for example, a polynucleotide (e.g., cDNA) encoding the correctly folded protein or an expression vector containing the polynucleotide. A gene encoding the MHC class II molecule may be a polynucleotide (e.g., cDNA) encoding the MHC class II molecule or an expression vector containing the polynucleotide, for example.

The method for introducing each coding gene is not particularly limited, and may be, for example, introduction using a gene gun such as a particle gun, a calcium phosphate method, a polyethylene glycol method, a lipofection method using liposome, an electroporation method, a nucleic acid introduction using ultrasonic waves, a DEAE-dextran method, a direct injection using a minute glass tube or the like, a hydrodynamic method, a cationic liposome method, a method using an adjuvant for helping introduction, and an *agrobacterium*-mediated method. Examples of the liposome include Lipofectamine® and cationic liposomes. Examples of the adjuvant for helping introduction include atelocollagen, nano-particles, and polymers.

The host cell is not particularly limited, and may be an animal cell, a plant cell, an insect cell, or the like, for example. The animal cell is not particularly limited, and examples thereof include: various cultured cells such as HeLa cells, 293 cells, 293T cells, NIH3T3 cells, COS cells, and CHO cells; stem cells such as ES cells and hematopoietic stem cells; immune cells such as T cells, B cells, dendritic cells, macrophages, and glial cells; and cells isolated from living organisms, such as primary cultured cells. Examples of the cell exclude human fertilized eggs and cells present in human embryos and human individuals. Examples of the host cell having a gene encoding the MHC class II molecule as an endogenous gene include the above-described immune cells.

It is only required that the polynucleotide be ligated functionally to the expression vector so that a protein encoded by the polynucleotide can be expressed in the host, for example, and other configurations of the expression vector are not particularly limited.

The expression vector can be prepared by inserting the polynucleotide to a vector that forms a main structure (also referred to as "basic vector" hereinafter), for example. The kind of the basic vector is not particularly limited, and can be determined as appropriate depending on the kind of the host, for example. When an animal cell is to be transformed, the basic vector may be pME18S, pCAGGS, or the like, for example.

The expression vector preferably has a regulatory sequence that regulates the expression of the polynucleotide, for example. The regulatory sequence may be, for example, a promoter, a terminator, an enhancer, a polyadenylation signal sequence, and a replication origin sequence (ori). The source of the promoter is not particularly limited, and examples thereof include cytomegalovirus (CMV), Rous sarcoma virus (RSV), simian virus-40 (SV-40), a muscle β-actin promoter, and herpes simplex virus (HSV). Other examples of the promoter include: tissue-specific promoters such as a thymidine kinase promoter; regulatory promoters such as a growth hormone regulatory promoter; promoters under the control of the lac operon sequence; and inducible promoters such as a zinc-inducible metallothionein promoter. In the expression vector, the arrangement of the regulatory sequence is not particularly limited. In the expression vector, it is only required that the regulatory sequence is arranged so that, for example, it can functionally regulate the expression of the polynucleotide and the expression of the subunit encoded by the polynucleotide, and the regulatory sequence can be arranged on the basis of a known method. As the regulatory sequence, a sequence previously provided in the basic vector may be used, or the regulatory sequence may be further inserted into the basic vector, for example. Alternatively, the regulatory sequence provided in the basic vector may be replaced with another regulatory sequence.

The expression vector further may contain a sequence encoding a selection marker, for example. The selection marker may be a drug-resistant marker, a fluorescent protein marker, an enzyme marker, a cell surface receptor marker, or the like, for example.

The method for culturing the host cell is not particularly limited, and can be determined as appropriate depending on the kind of the host cell.

As described above, by introducing the gene encoding a correctly folded protein into the MHC class II molecule expression system cell, it is possible to obtain a cell presenting the denatured protein/MHC class II.

In the present invention, for example, a cell presenting the denatured protein/MHC class II may be used as it is as an antigen reagent. Alternatively, the denatured protein/MHC class II dissociated from the cell presenting the denatured protein/MHC class II may be used as an antigen reagent, or the denatured protein dissociated from a complex of the denatured protein and the MHC class II molecule may be used as an antigen reagent. In these cases, it is preferable to purify the denatured protein/MHC class II from the cell or to purify the denatured protein from the denatured protein/MHC class II, for example. The purification method is not particularly limited, and a known method can be used. The purification method may be, for example, salting-out, ion exchange chromatography, affinity chromatography, gel filtration chromatography, or the like.

The present invention may include, prior to the contact step, the above described step of preparing the denatured protein/MHC class II, and further may include the step of purifying the denatured protein/MHC class II.

In the present invention, the antigen reagent may include only the denatured protein/MHC class II, or may further include a component(s) other than the denatured protein/MHC class II, for example. The antigen reagent may include one kind of denatured protein/MHC class II or two or more kinds of denatured protein/MHC class II in combination, for example.

The denatured protein/MHC class II may be used in a free state or in a state of being immobilized on a carrier, for example. In the latter case, the antigen reagent includes the carrier as the other component, for example. The carrier is not particularly limited, and examples thereof include plates such as a well plate and beads.

The other component may be, for example, water, physiological saline, a buffer solution, buffered saline, a medium, or the like.

(3) Contact Step

In the present invention, the contact step is the step of causing the sample and the antigen reagent containing the denatured protein/MHC class II to come into contact with each other.

The sample is not particularly limited, and examples thereof include specimens that may contain an autoantibody, such as a biological specimen, for example. The biological specimen is not particularly limited, and may be blood, body fluid, a tissue, or the like. The blood specimen may be whole blood, serum, plasma, or the like, for example. The body fluid specimen is not particularly limited, and may be synovial fluid, urine, saliva, or the like, for example. The tissue specimen is not particularly limited, and may be a target tissue of the autoimmune disease, for example. Specific examples thereof include the thyroid, pancreas, blood vessels, cerebrum, cerebellum, spinal cord, ophthalmic nerve, joints, bones, salivary gland, synovial membrane, heart, and liver. The source of the sample is not particularly limited, and examples thereof include humans and non-human animals excluding humans. The non-human animals are as described above, for example.

The sample may be either liquid or solid, for example, and preferably is in the form of liquid from the viewpoint of ease of handling, for example. When the specimen is liquid, the specimen may be used as a liquid sample as it is without being diluted. Alternatively, a diluted solution obtained by suspending, dispersing, or dissolving the specimen in a medium may be used as the sample, for example. When the specimen is solid, a diluted solution obtained by suspending, dispersing, or dissolving the specimen in a medium preferably is used as the sample, for example. The medium is not particularly limited, and may be water, physiological saline, a buffer solution, buffered saline, or the like, for example. The buffer solution is not particularly limited, and examples thereof include a Tris buffer solution, a phosphate buffer solution, an acetate buffer solution, a borate buffer solution, a citrate buffer solution, a veronal buffer solution, and various Good's buffer solutions.

In the contact step, the antigen reagent may be added to the sample, or the sample may be added to the antigen reagent, for example. The ratio between the sample and the antigen reagent to be added is not particularly limited. Specifically, when serum is used as the sample, it is preferable to use cells presenting the denatured protein/MHC class II as the antigen reagent. The ratio between the serum and the cells to be added is not particularly limited, and may be as follows, for example: with respect to 1,000 to 20,000,000 (e.g., about 5,000,000) cells, 0.01 to 1 ml of the serum is to be added. It is preferable to add the serum in the form of a diluted serum sample obtained by diluting the serum 50- to 10,000-fold (e.g., about 300-fold), for example.

In the contact step, it is preferable to incubate the sample and the antigen reagent for a certain time period after they were brought into contact with each other, for example. The conditions for the incubation are not particularly limited, and may be as follows: the temperature is, for example, 0° C. to 37° C., preferably 0° C. to 10° C., and more preferably 0° C. to 5° C.; the pH is, for example, 6 to 9, preferably 7 to 8, and more preferably 7.2 to 7.6; and the time period is, for example, 3 to 120 minutes, preferably 10 to 90 minutes, and more preferably 30 to 60 minutes.

(4) Detection Step

In the present invention, the detection step is the step of detecting a complex of an autoantibody in the sample and the denatured protein in the antigen reagent. In the detection step, it is possible to check the presence or absence of the complex (qualitative analysis) or to measure the amount of the complex (quantitative analysis), for example. Because the complex contains the autoantibody, the autoantibody can be detected indirectly by detecting the complex.

The form of the complex may be changed depending on the form of the denatured protein/MHC class II in the antigen reagent, for example. When the antigen reagent includes cells presenting the denatured protein/MHC class II, the complex may be a complex of the autoantibody and the cell presenting the denatured protein/MHC class II, for example. When the antigen reagent includes the denatured protein/MHC class II dissociated from the cell, the complex may be a complex of the autoantibody and the denatured protein/MHC class II, for example. When the antigen reagent includes the denatured protein dissociated from the MHC class II molecule, the complex may be a complex of the autoantibody and the denatured protein, for example. It is preferable that these complexes are all formed through the binding of the autoantibody and the denatured protein, for example.

In the detection step, the method for detecting the complex is not particularly limited. The detection method may be a method in which, for example, a substance for detecting the autoantibody in the complex is used, and the complex is detected indirectly by measuring the detecting substance.

The detecting substance may be, for example, a secondary antibody that binds to the autoantibody (primary antibody), such as a polyclonal antibody. The secondary antibody preferably is labeled with a labeling substance, for example. The labeling substance is not particularly limited, and may be a fluorescent substance, a dye, an isotope, an enzyme, or the like, for example. Examples of the fluorescent substance include fluorophores such as pyrene, TAMRA, fluorescein, a Cy3 dye, and a Cy5 dye. Examples of the dye include Alexa dyes such as Alexa 488. Examples of the isotope include stable isotopes and radioisotopes, and stable isotopes are preferable. The enzyme is not particularly limited, and examples thereof include horseradish-derived peroxidase, alkaline phosphatase, and luciferase. When the labeling substance is an enzyme, it is preferable to use a substrate for the enzyme in combination, for example. As the substrate, it is preferable to use a substance that emits fluorescence, light, or the like through a catalytic reaction of the enzyme, for example.

The substrate is not particularly limited, and examples thereof include hydrogen peroxide, 3,3',5,5'-tetramethylbenzidine (TMB), 1,2-phenylenediamine (OPD), 2,2'-azinobis (3-ethylbenzothiazoline-6-sulfonic acid) ammonium salt (ABTS), 3,3'-diaminobenzidine (DAB), 3,3'-diaminobenzidine tetrahydrochloride hydrate (DAB4HCl), 3-amino-9-ethylcarbazole (AEC), 4-chloro-1-naphthol (4C1N), 2,4,6-tribromo-3-hydroxybenzoic acid, 2,4-dichlorophenol, 4-aminoantipyrine, 4-aminoantipyrine hydrochloride, luminol, and luciferin.

The detection method can be selected as appropriate depending on the form of the complex, for example. When the complex is a complex of the autoantibody and a cell presenting the denatured protein/MHC class II, the complex can be detected by means of, for example, flow cytometry, a device for measuring fluorescence intensities, a fluorescence microscope, or the like.

In the detection step, the conditions for the detection are not particularly limited, and can be determined as appropriate depending on the detection method.

(Test Method for Testing Possibility of Autoimmune Disease)

The test method for testing the possibility of an autoimmune disease according to the present invention is, as described above, a test method for testing a possibility of an autoimmune disease, wherein a sample is a biological specimen isolated from a subject, including the steps of: detecting a complex of an autoantibody in the sample and a denatured protein presented by an MHC class II molecule (the denatured protein/MHC class II) by the detection method according to the present invention; and evaluating the possibility of the autoimmune disease from the result of detecting the complex in the detection step.

The test method of the present invention is characterized in that an autoantibody in the biological specimen is detected indirectly by detecting the complex by the detection method of the present invention, and other steps and conditions are not particularly limited. According to the test method of the present invention, it is possible to detect an autoantibody with high accuracy, thus allowing the possibility of an autoimmune disease to be tested with high accuracy. Regarding the test method of the present invention, reference can be made to the above description concerning the detection method of the present invention, unless otherwise stated.

In the test method of the present invention, the subject is not particularly limited, and examples thereof include humans and non-human animals excluding humans. The non-human animals are as described above, for example.

In the test method of the present invention, the autoimmune disease to be tested is not particularly limited, and examples thereof include rheumatoid arthritis, Hashimoto's disease, Basedow's disease (Graves' disease), anti-phospholipid antibody syndrome, insulin autoimmune syndrome, pemphigus, bullous pemphigoid, scleroderma, Sjogren's syndrome, Goodpasture's syndrome, membranous nephropathy, IgA nephropathy, systemic lupus erythematosus (lupus erythematosus), dilated cardiomyopathy, IgG4-related disease, ANCA-associated vasculitis, myasthenia gravis, Harada disease, narcolepsy, Buerger's disease, type I diabetes, multiple sclerosis, neuromyelitis optica, primary biliary cirrhosis, Crohn's disease, ulcerative colitis, mixed connective-tissue disease, Wegener's granulomatosis, vilitigo vulgaris, multiple myositis/dermatitis, idiopathic thrombocytopenic purpura (ITP), idiopathic Addison's disease, idiopathic autoimmune hepatitis, autoimmune pancreatitis, atrophic gastritis, primary sclerosing cholangitis, aortitis syndrome (Takayasu's arteritis), autoimmune hemolytic anemia, autoimmune inner ear disorder, idiopathic azoospermia, acute disseminated encephalomyelitis, alopecia areata, autoimmune cardiomyopathy, chronic inflammatory demyelinating polyradiculoneuropathy, Churg-Strauss syndrome, idiopathic pulmonary fibrosis, Guillain-Barre syndrome, lichen sclerosus, microscopic polyangiitis, paroxysmal nocturnal hemoglobinuria, relapsing polychondritis, sarcoidosis, and Stiff person syndrome. Specific examples of the relationship of the autoimmune diseases with the denatured proteins and the MHC class II are shown in Table 1 above, for example.

As described above, specific examples are as follows: in the case of a test for rheumatoid arthritis, the MHC class II molecules include HLA-DR and the denatured protein is a denatured protein resulting from denaturation of an IgG heavy chain, for example; in the case of a test for Hashimoto's disease, the MHC class II molecules include HLA-DR and the denatured protein is a denatured protein resulting from denaturation of thyroglobulin, for example; in the case of a test for anti-phospholipid antibody syndrome, the MHC class II molecules include HLA-DR and the denatured protein is a denatured protein resulting from denaturation of β2-glycoprotein I, for example; and in the case of a test for Basedow's disease, the MHC class II molecules include HLA-DP and the denatured protein a denatured protein resulting from denaturation of TSHR, for example.

As described above, the detection step is the step of detecting a complex of an autoantibody in the biological specimen and the denatured protein/MHC class II by the autoantibody detection method of the present invention. Because the complex contains the autoantibody, the autoantibody in the biological specimen can be detected indirectly by detecting the complex.

The detection step may be, for example, the step of measuring the amount of complex formation, as described above. The method for measuring the amount of complex formation is not particularly limited, and any of the above-described methods for detecting the complex can be employed, for example. The method for determining the amount of the autoantibody indirectly from the amount of complex formation is not particularly limited. For example, it is possible to utilize a relational expression (including a calibration curve, for example) or the like showing the relationship between the measured value of the complex and the amount of the autoantibody. The relational expression can be obtained in the following manner, for example: by performing detection of a complex with respect to standard samples containing known amounts of the autoantibody according to the detection method, it is possible to determine a relational expression showing the relationship between the measured values of the complex and the known amounts of the autoantibody. On the basis of this relational expression, the amount of the autoantibody can be calculated from the measured value of the amount of complex formation. Thus, in the present invention, "the amount of complex formation" also can be referred to as "the amount of the autoantibody" calculated indirectly from the amount of complex formation, for example.

The evaluation step is the step of evaluating the possibility of the autoimmune disease from the result of detecting the complex in the detection step, as described above. The result of detecting the complex can be referred to as the result of indirectly detecting the autoantibody, for example. Because the autoantibody can be a sign of the autoimmune disease, it is possible to determine that, for example, the subject has a possibility of the autoimmune disease or does not have a possibility of the autoimmune disease, from the result of detecting the complex, i.e., the result of indirectly detecting the autoantibody. When the subject has a possibility of the autoimmune disease, it means that, for example, the subject is affected with the autoimmune disease presently, the subject may be affected with the autoimmune disease presently, and the subject may be affected with (also referred to as "may develop") the autoimmune disease in the future. When the subject does not have a possibility of the autoimmune disease, it means that, for example, the subject is not affected with the autoimmune disease presently and the subject may not be affected with the autoimmune disease presently (the same applies hereinafter).

In the evaluation step, the possibility of the autoimmune disease in the subject can be determined as follows, for example: when the complex is detected in the detection step, it can be determined that the subject has a possibility of the autoimmune disease, and when the complex is not detected in the detection step, it can be determined that the subject does not have a possibility of the autoimmune disease.

In the evaluation step, the possibility of the autoimmune disease in the subject also can be determined by comparing the measured value of the amount of complex formation in the subject obtained in the measurement step with a reference value, for example. Specifically, for example, the measured value is compared with the reference value in the evaluation step, and when the measured value is higher than the reference value, it can be determined that the subject has a possibility of the autoimmune disease, whereas, when the measured value is lower than the reference value, it can be determined that the subject does not have a possibility of the autoimmune disease.

The reference value is not particularly limited, and may be the amount of complex formation in a biological specimen of a healthy donor not affected with the autoimmune disease, for example. In the case where the amount of an autoantibody calculated from the measured value of the amount of complex formation is to be compared with the reference value, it is preferable that the amount of complex formation in the healthy donor also is the amount of the autoantibody. The biological specimen of the healthy donor preferably is the one isolated under the same conditions as those for the biological specimen of the subject, for example. The amount of complex formation in the biological specimen of the healthy donor preferably is detected in the same manner and under the same conditions as those for the detection with respect to the biological specimen of the subject, for example.

The above description is directed to an example where the possibility of the autoimmune disease is determined on the precondition that, in the comparison of the measured value with the reference value, the measured value obtained when the complex is formed is a positive value. It is to be noted, however, that the measured value obtained when the complex is formed may be a negative value. In this case, for example, the measured value is compared with a reference value in the evaluation step, and when the measured value is lower than the reference value, it can be determined that the subject has a possibility of the autoimmune disease, whereas, when the measured value is higher than the reference value, it can be determined that the subject does not have a possibility of the autoimmune disease.

(Diagnostic Method for Autoimmune Disease)

The above-described method for testing the possibility of an autoimmune disease according to the present invention also can be referred to as a diagnostic method for an autoimmune disease, for example. That is, the diagnostic method for an autoimmune disease according to the present invention is, as described above, a diagnostic method wherein a sample is a biological specimen isolated from a subject, including the steps of; detecting a complex of an autoantibody in the sample and a denatured protein presented by an MHC class II molecule (the denatured protein/MHC class II) by the detection method according to the present invention; and diagnosing the autoimmune disease from the result of detecting the complex in the detection step.

Regarding the diagnostic method of the present invention, reference can be made to the above description concerning the test method of the present invention. In the diagnostic method of the present invention, the test for the possibility of an autoimmune disease in the test method means the diagnosis of whether the subject is affected with the autoimmune disease.

(Autoantibody Detection Reagent)

As described above, the autoantibody detection reagent of the present invention is an autoantibody detection reagent for use in the autoantibody detection method of the present invention, including a denatured protein presented by an MHC class II molecule.

The detection reagent of the present invention is characterized in that it includes the denatured protein/MHC class II as an antigen reagent against an autoantibody, and other configurations and conditions are not particularly limited. Regarding the detection reagent of the present invention, reference can be made to the above description concerning the antigen reagent in the detection method of the present invention. According to the detection reagent of the present invention, it is possible to detect an autoantibody with high accuracy.

The autoantibody detection reagent of the present invention can be used for detection of the autoantibody, for example, and it is possible to diagnose an autoimmune disease from the result of detecting the autoantibody, as described above. Thus, the autoantibody detection reagent of the present invention also can be referred to as an autoimmune disease diagnostic reagent.

(Method for Producing Autoantibody Detection Reagent)

As described above, the method for producing an autoimmune disease detection reagent according to the present invention includes the step of: preparing an MHC class II molecule presenting a denatured protein resulting from denaturation of a correctly folded protein by introducing a gene encoding the correctly folded protein into an MHC class II molecule expression system cell. Regarding the production method of the present invention, reference can be made to the above description concerning the production of the antigen reagent in the detection method of the present invention.

(Screening Method for Antigen Protein Against Autoantibody Relevant to Autoimmune Disease)

The screening method of the present invention is a screening method for an antigen protein against an autoantibody relevant to an autoimmune disease, wherein, as described above, a sample is a biological specimen isolated from a subject affected with an autoimmune disease, including the steps of; detecting a complex of an autoantibody in the sample and a denatured protein presented by an MHC class II molecule by the detection method according to the present invention; and determining the denatured protein that has formed the complex with the autoantibody as an antigen protein against an autoantibody relevant to the autoimmune disease.

According to the screening method of the present invention, it is possible to select an antigen protein against an autoantibody relevant to an autoimmune disease through screening. As described above, a conventional autoantibody detection method using a correctly folded protein resulting from correct folding as an antigen reagent has a problem of occurrence of false negative in autoimmune disease patients. Thus, even if screening is performed using the correctly folded protein as an autoantigen candidate protein, there is a possibility that screening for an autoantigen that exhibits highly reliable association with the autoimmune disease actually may not be achieved. In contrast, by using the denatured protein presented by an MHC class II molecule as an autoantigen candidate protein, it becomes possible to achieve screening for an autoantigen that exhibits highly reliable association with the autoimmune disease, for example.

Regarding the screening method of the present invention, reference can be made to the above descriptions concerning the detection method of the present invention, the test method of the present invention, etc., unless otherwise stated.

In the screening method of the present invention, the type of the autoimmune disease is not particularly limited. The autoimmune disease may be, for example, an autoimmune disease for which an autoantigen has not been identified or an autoimmune disease for which an autoantigen has been presumed or identified.

As described above, the detection step is the step of detecting a complex of an autoantibody in the sample and the denatured protein/MHC class II by the autoantibody detection method of the present invention. The detection step may be, for example, the step of measuring the amount of complex formation, as described above.

As described above, the determination step is the step of determining the denatured protein that has formed the complex with the autoantibody as an antigen protein against an autoantibody relevant to the autoimmune disease. In the determination step, it can be determined that the denatured protein is the antigen protein when the complex is detected in the detection step, and it can be determined that the denatured protein is not the antigen protein when the complex is not detected in the detection step, for example.

In the evaluation step, whether the denatured protein is the antigen protein also can be determined by comparing the measured value of the amount of complex formation in the subject obtained in the measurement step with a reference value, for example. Specifically, for example, the measured value is compared with the reference value in the evaluation step, and when the measured value is higher than the reference value, it can be determined that the denatured protein is the antigen protein, whereas, when the measured value is lower than the reference value, it can be determined that the denatured protein is not the antigen protein.

The reference value is not particularly limited, and may be the amount of complex formation in a biological specimen of a healthy donor not affected with the autoimmune disease, for example. In the case where the amount of an autoantibody calculated from the measured value of the amount of complex formation is to be compared with the reference value, it is preferable that the amount of complex formation in the healthy donor also is the amount of the autoantibody. The biological specimen of the healthy donor preferably is the one isolated under the same conditions as those for the biological specimen of the subject, for example. The amount of complex formation in the biological specimen of the healthy donor preferably is detected in the same manner and under the same conditions as those for the detection with respect to the biological specimen of the subject, for example.

The above description is directed to an example where whether the denatured protein is the antigen protein is determined on the precondition that, in the comparison of the measured value with the reference value, the measured value obtained when the complex is formed is a positive value. It is to be noted, however, that the measured value obtained when the complex is formed may be a negative value. In this case, for example, the measured value is compared with a reference value in the determination step, and when the measured value is lower than the reference value, it can be determined that the denatured protein is the antigen protein, whereas, when the measured value is higher than the reference value, it can be determined that the denatured protein is not the antigen protein.

EXAMPLES (1) Preparation of Expression Vectors (1-1) HLA-DR Expression Vectors, HLA-DP Expression Vectors From cDNAs in human peripheral-blood mononuclear cells (3H Biomedical) or a human cell line, polynucleotides encoding an α-chain and β-chains of HLA-DR shown in Tables 2A and 2B below or an α-chain and β-chains of HLA-DP shown in Tables 3A and 3B below were cloned into pME18S vectors, respectively. The sequence information on the cDNA of HLA-DR was obtained from the IMGT/HLA Database (http://www.ebi.ac.uk/imgt/hla/index/html). Hereinafter, the expression vectors prepared by the above-described cloning are indicated with the gene names shown in the tables below (the same applies hereinafter).

TABLE 2A

| Example | MHC class II α-chain (HLA-DRA) Gene name | IMGT/HLA Accession No. |
|---|---|---|
| 1A-1G, 2A-2E, 3A-3D | HLA-DRA*01:01 | HLA00662 |

TABLE 2B

| Example | MHC class II β-chain (HLA-DRB) Gene name | IMGT/HLA Accession No. |
|---|---|---|
| 1F, 2A, 2C-2E, 3B | HLA-DRB1*01:01 | HLA00664 |
| 1F, 2A, 3B | HLA-DRB1*01:03 | HLA00667 |
| 1B, 1E, 1F, 3B | HLA-DRB1*03:01 | HLA00671 |
| 3B | HLA-DRB1*03:04 | HLA00676 |
| 3B | HLA-DRB1*03:08 | HLA00680 |
| 3B | HLA-DRB1*03:16 | HLA01152 |
| 1E, 1F, 3B | HLA-DRB1*04:01 | HLA00685 |
| 1F, 3B | HLA-DRB1*04:02 | HLA00687 |
| 1F, 2A, 3B | HLA-DRB1*04:03 | HLA00688 |
| 1A-1D, 1F, 1G, 3A, 3B | HLA-DRB1*04:04 | HLA00689 |
| 3B | HLA-DRB1*04:05 | HLA00690 |
| 3B | HLA-DRB1*04:06 | HLA00692 |
| 1F, 3B-3D | HLA-DRB1*07:01 | HLA00719 |
| 1F, 3B, 3C | HLA-DRB1*08:01 | HLA00723 |
| 3B | HLA-DRB1*08:03 | HLA00727 |
| 1F, 3B | HLA-DRB1*09:01 | HLA00749 |
| 1F, 3B | HLA-DRB1*10:01 | HLA00750 |
| 1F, 3B | HLA-DRB1*11:01 | HLA00751 |
| 1F, 3B | HLA-DRB1*12:01 | HLA00789 |
| 1F, 3B | HLA-DRB1*13:01 | HLA00797 |
| 1F, 3B | HLA-DRB1*13:02 | HLA00798 |
| 1F, 3B | HLA-DRB1*13:03 | HLA00799 |
| 1F, 3B | HLA-DRB1*14:01 | HLA00833 |
| 3B | HLA-DRB1*14:02 | HLA00834 |
| 2A, 3B | HLA-DRB1*14:03 | HLA00835 |
| 2A | HLA-DRB1*14:05 | HLA00837 |
| 3B | HLA-DRB1*14:06 | HLA00838 |
| 1E, 1F, 2A, 3B | HLA-DRB1*15:01 | HLA00865 |
| 3B | HLA-DRB3*02:02 | HLA00895 |
| 2A-2E, 3B | HLA-DRB4*01:03 | HLA00908 |

TABLE 3A

| Example | MHC class II α-Chain (HLA-DPA) Gene name | IMGT/HLA Accession No. |
|---|---|---|
| 4 | HLA-DPA1*02:02 | HLA00508 |

TABLE 3B

| Example | MHC class II β-Chain (HLA-DPB) Gene name | IMGT/HLA Accession No. |
|---|---|---|
| 4 | HLA-DPB1*05:01 | HLA00523 |

(1-2) Antigen Protein Expression Vectors

From mouse spleen cDNA, polynucleotides encoding a secretory IgG heavy chain, a membrane IgG heavy chain, an IgG light chain, Igα, and Id shown in Table 4 below were cloned into pME18S vectors, respectively. From human thyroid cDNA, a polynucleotide encoding thyroglobulin shown in Table 4 below was cloned into a pME18S vector. From human peripheral blood mononuclear cell cDNA, a polynucleotide encoding β2-glycoprotein I (β2-GPI) shown in Table 4 below was cloned into a pME18S vector. From human thyroid cDNA, a thyroid-stimulating hormone receptor (TSHR) shown in Table 4 below was cloned into a pME18S vector.

TABLE 4

| Corresponding Example | Gene name | Accession No. or Base sequence |
|---|---|---|
| 1A-1G | mouse secretory IgG heavy chain (sIgGH) | JQ917464 |
| 1C | mouse membrane IgG heavy chain (mIgGH) | SEQ ID NO: 1 |
| 1C, 1D | mouse IgG light chain (IgGL) | JQ917465 |
| 1C | mouse Igα | NM_007655.3 |
| 1C | mouse Igβ | NM_008339.2 |
| 2A-2E | human thyroglobulin (TG) | NM_003235.4 |
| 3A-3D | human β2-GPI | NM_000042.2 |
| 4 | human TSHR | AY429111 |

*: Mouse secretory IgG heavy chain (sIgGH) and mouse membrane IgG heavy chain (mIgGH) have the same V region.

```
Mouse membrane IgG heavy chain (mIgGH)
                                  (SEQ ID NO: 1)
GTCTTGTCCCAGGTCACCTTGAAGGAGTCTGGTCCTGTGCTGGTGAAA

CCCACAGAGACCCTCACGCTGACCTGCAGCGTCTCTGGGTTCTCACTC

AGCAACGGTAGAATGGGTGTGAGTTGGATCCGTCAGCCCCCAGGGAAG

GCCCTGGAGTGGGTTGGACACATTTTTTCGAATGACGACAAATCTTAC

ACCCCATCTCTGGAGAGCAGGCTCACCATCTCCCAGGACACCTTCAGA

AGCCAGGTGGTCCTAACCATTACCAACTTGGCCCCCGTGGACACAGGC

ACATATTATTGTGCACGAATAAGTCGTTCCATTTATGGGGTGCTTACC

CCCGGCAGCGTCTGGGGCCAAGGGACCATGGTCACCGTCTCCTCAGCC

TCCACCAAGGGCCCATCGGTCTTCCCCCTGGCACCCTCCTCCAAGAGC

ACCTCTGGGGGCACAGCGGCCCTGGGCTGCCTGGTCAAGGACTACTTC

CCCGAACCGGTGACGGTGTCGTGGAACTCAGGCGCCCTGACCAGCGGC

GTGCACACCTTCCCGGCTGTCCTACAGTCCTCAGGACTCCACTCCCTC

AGCAGCGTGGTGACCGTGCCCTCCAGCAGCTTGGGCACCCAGACCTAC

ATCTGCAACGTGAATCACAAGCCCAGCAACACCAAGGTGGACAAGAAA

GTTGAGCCCAAATCTTGTGACAAAACTCACACATGCCCACCGTGCCCA

GCACCTGAACTCCTGGGGGGACCGTCAGTCTTCCTCTTCCCCCCAAAA

CCCAAGGACACCCTCATGATCTCCCGGACCCCTGAGGTCACATGCGTG

GTGGTGGACGTGAGCCACGAAGACCCTGAGGTCAAGTTCAACTGGTAC

GTGGACGGCGTGGAGGTGCATAATGCCAAGACAAAGCCGCGGGAGGAG

CAGTACAACAGCACGTACCGTGTGGTCAGCGTCCTCACCGTCCTGCAC

CAGGACTGGCTGAATGGCAAGGAGTACAAGTGCAAGGTCTCCAACAAA

GCCCTCCCAGCCCCCATCGAGAAAACCATCTCCAAAGCCAAAGGGCAG

CCCCGAGAACCACAGGTGTACACCCTGCCCCCATCCCGGGATGAGCTG

ACCAAGAACCAGGTCAGCCTGACCTGCCTGGTCAAAGGCTTCTATCCC

AGCGACATCGCCGTGGAGTGGGAGAGCAATGGGCAGCCGGAGAACAAC

TACAAGACCACGCCTCCCGTGCTGGACTCCGACGGCTCCTTCTTCCTC

TACAGCAAGCTCACCGTGGACAAGAGCAGGTGGCAGCAGGGGAACGTC
```

-continued

```
TTCTCATGCTCCGTGATGCATGAGGCTCTGCACAACCACTACACGCAG

AAGAGCCTCTCCCTGTCCCCGGAGCTGCAACTGGAGGAGAGCTGTGCG

GAGGCGCAGGACGGGGAGCTGGACGGGCTGTGGACGACCATCACCATC

TTCATCACACTCTTCCTGTTAAGCGTGTGCTACAGTGCCACCGTCACC

TTCTTCAAGGTGAAGTGGATCTTCTCCTCGGTGGTGGACCTGAAGCAG

ACCATCATCCCCGACTACAGGAACATGATCGGACAGGGGCCTAG
```

(1-3) Other Vectors

A polynucleotide encoding Cw3-pep-HLA-DRB1*04:04, which is HLA-DRB1*04:04 shown in Table 1 with a linker peptide (SEQ ID NO: 2: GSGSGS) and a Cw3 peptide (SEQ ID NO: 3: GSHSMRYFYTAVSRPGR) bound thereto, was cloned into a pME18S vector in the manner described in the following literature. This vector inhibits the binding properties of the peptide-binding groove of HLA-DR.

Literature: Scott, C. A. et al., I. A. Crystal structures of two I-Ad-peptide complexes reveal that high affinity can be achieved without large anchor residues. Immunity 8, pp. 319-329, (1998)

From human peripheral blood mononuclear cell cDNA, a polynucleotide encoding an invariant chain shown in Table 5 below was cloned into a pME18S vector.

A polynucleotide represented by SEQ ID NO: 4, which encodes GFP, was cloned into a pME18S vector.

TABLE 5

| Corresponding Example | Gene name | Accession No. or SEQ ID NO: |
| --- | --- | --- |
| 1F | human invariant chain (Ii) | NM_004355.2 |
| 1A, 1C-1G, 2A, 2C-2E, 3A, 3B, 3D, 4 | GFP | SEQ ID NO: 4 |

GFP (SEQ ID NO: 4)
```
atggtgagcaagggcgaggagctgttcaccggggtggtgcccatcctg gtcgagctggacggcgacgtaaacggccacaagttcagcgtgtccggc gagggcgagggcgatgccacctacggcaagctgaccctgaagttcatc tgcaccaccggcaagctgcccgtgccctggcccaccctcgtgaccacc ctgacctacggcgtgcagtgcttcagccgctaccccgaccacatgaag cagcacgacttcttcaagtccgccatgcccgaaggctacgtccaggag cgcaccatcttcttcaaggacgacggcaactacaagacccgcgccgag gtgaagttcgagggcgacaccctggtgaaccgcatcgagctgaagggc atcgacttcaaggaggacggcaacatcctggggcacaacatggagtac aactacaacagccacaacgtctatatcatggccgacaagcagaagaac ggcatcaaggtgaacttcaagatccgccacaacatcgaggacggcagc gtgcagtcgccgaccactaccagcagaacacccccatcggcgacggcc ccgtgctgctgcccgacaaccactacctgagcacccagtccgccctga gcaaagaccccaacgagaagcgcgatcacatggtcctgctggagttcg tgaccgccgcgggatcactctcggcatggacgagctgtacaagtaa
```

(2) Introduction of Expression Vectors 293T cells (RIKEN BioResource Center) were used as host cells to which the above-described expression vectors were to be introduced. As a transfection reagent, a PEI max (trade name, Polysciences, Inc.) was used. For introduction of each expression vector into the 293T cell, a PEI max solution obtained by dissolving the PEI max (Cosmo Bio Co., Ltd.) in purified water at a concentration of 2 mg/ml was used. Specifically, the expression vector was introduced in accordance with the instructions for use of a Lipofectamine® 2000 (Invitrogen), using the PEI max solution instead of the Lipofectamine® 2000. The 293T cells were cultured at 37° C. for two days using a DMEM medium.

(3) Reagents

It should be interpreted that reagents, such as antibodies, indicated with the same names are the same products, unless otherwise stated.

Example 1

Example 1 relates to the detection of an autoantibody as an indicator of rheumatoid arthritis.

Example 1A

In the present example, HLA-DR and an IgG heavy chain were expressed, and whether the IgG heavy chain was presented on cell surfaces by the HLA-DR was examined.

The HLA-DRA*01:01 vector as an α-chain expression vector, the HLA-DRB1*04:04 vector as a β-chain expression vector, the sIgGH vector for secretory IgG heavy chain expression, and the GFP vector were introduced to 293T cells, and the 293T cells were cultured. The cultured cells were reacted with an allophycocyanin (APC)-labeled anti-human IgG Fc antibody or anti-HLA-DR antibody, and further reacted with an APC-labeled anti-mouse IgG antibody. Thereafter, the cells were subjected to flow cytometry analysis. Specifically, using a flow cytometer (trade name; FACS Calibur™, Becton Dickinson), IgG heavy chain expression and HLA-DR expression on surfaces of GFP-positive cells were examined. As Control 1, the analysis was performed in the same manner, except that the HLA-DR expression vectors were not introduced. As Control 2, the analysis was performed in the same manner, except that the Cw3-pep-HLA-DRB1*04:04 vector was introduced instead of the HLA-DR expression vectors. The Cw3-pep-HLA-DRB1*04:04 vector can inhibit the binding of the IgG heavy chain to the peptide-binding groove of the HLA-DR.

APC-labeled anti-human IgG Fc antibody: available from Jackson ImmunoResearch, Code: 109-136-098 anti-HLA-DR antibody for flow cytometry: Clone HL-40, available from EXBIO, monoclonal antibody (mAb)

APC-labeled anti-mouse IgG antibody: available from Jackson ImmunoResearch, Code: 715-136-150

The results obtained are shown in FIG. 1. FIG. 1 shows histograms respectively showing the expression levels of the IgG and the HLA-DR on the cell surfaces. In FIG. 1, the horizontal axis indicates the fluorescence intensity, which shows the expression level of the IgG presented on the HLA-DR or the expression level of the HLA-DR, and the vertical axis indicates the cell counts. As can be seen in FIG. 1, in the cells (HLA-DR0404) to which the HLA-DRA*01:01, the HLA-DRB1*04:04, and the IgG heavy chain had been introduced, IgG expression and HLA-DR expression were observed on the cell surfaces. In contrast, in Control 1 (without HLA-DR), IgG expression and HLA-DR expression on the cell surfaces were not observed, and in Control 2 (Cw3-pep-HLA-DR0404), although HLA-DR expression on the cell surfaces was observed, the expression level of the IgG on the cell surfaces was low. From these results, it was found that HLA-DR is necessary for IgG heavy chain expression on a cell surface and that an IgG heavy chain is presented on a cell surface with being bound to the peptide-binding groove of HLA-DR. IgG is a homodimer composed of heavy chains and light chains, and it is known that, unless both the heavy chains and the light chains are present, correct folding of IgG does not occur, so that IgG does not function as an antibody. In the present example, only the IgG heavy chain was introduced to the cells, and in the absence of light chain, only the heavy chain was expressed on the cell surfaces by the HLA-DR. Thus, it can be said that the IgG presented on the cell surfaces is a misfolded protein (denatured protein).

Example 1B

In the present example, HLA-DR was immunoprecipitated, and whether an IgG heavy chain was bound to the peptide-binding groove of the HLA-DR was examined.

To 293T cells, the HLA-DRA*01:01 as an α-chain expression vector and the other respective expression vectors were introduced so as to achieve the combinations shown in FIG. 2 to be described below. The 293T cells were then cultured. The cultured cells were lysed in a 0.5% NP-40 solution (polyoxyethylene(9)octyiphenyl ether), and the resultant cell lysate was immunoprecipitated using a biotinylated anti-HLA-DR antibody and streptavidin sepharose (GE Healthcare).

biotinylated anti-HLA-DR antibody for immunoprecipitation: Clone L243, available from ATCC, mAb Western blotting was performed on the immunoprecipitated sample. Specifically, the sample was applied to electrophoresis, and IgG and HLA-DR were detected using a peroxidase-labeled anti-human IgG antibody or a rabbit anti-HLA-DR α antibody and a peroxidase-labeled anti-rabbit IgG antibody. As a control, Western blotting was performed in the same manner, except that the cell lysate was immunoprecipitated using Protein A Sepharose (GE Healthcare).

peroxidase-labeled anti-rabbit IgG antibody: available from Thermo Fisher Scientific, Prod#: 1858415
    peroxidase-labeled anti-human IgG antibody: available from Jackson ImmunoResearch, Code: 709-035-149
    rabbit anti-HLA-DRα antibody: Product No. FL-254, available from Santa Cruz Biotechnology, Inc.

Figure 2:
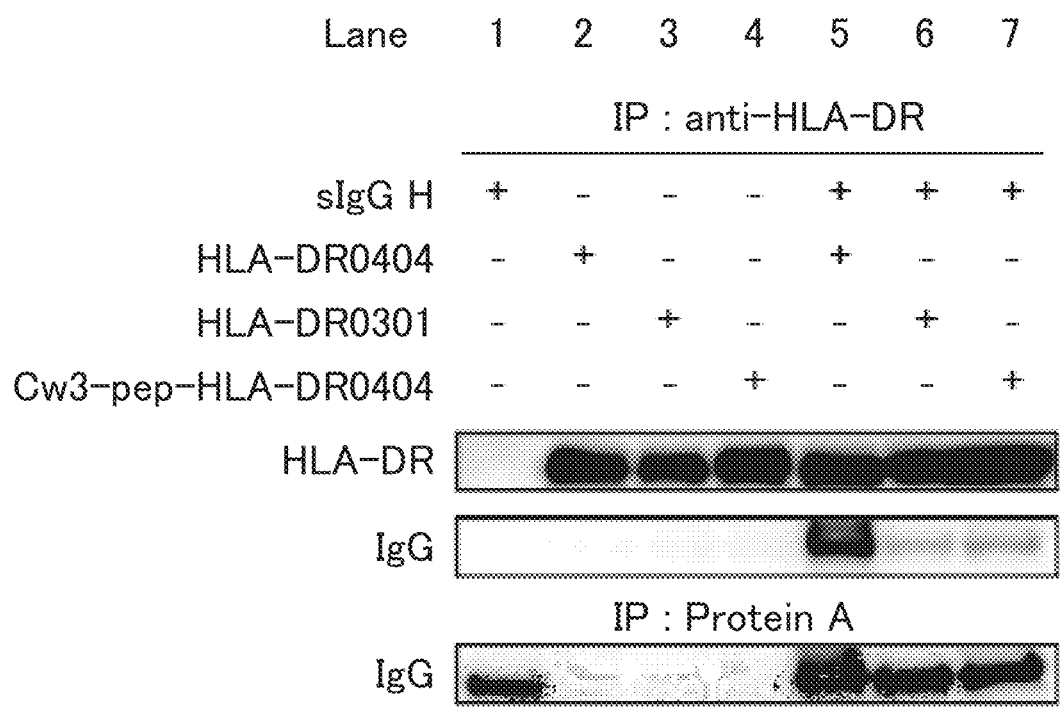
FIG. 2 shows Western blot photographs showing the binding between IgG and MHC class II molecules in Example 1B.

The results obtained are shown in FIG. 2. FIG. 2 shows Western blot photographs. In FIG. 2, lane numbers and whether the expression vector had been introduced (+) or had not been introduced (−) are shown above the photographs, and the kinds of the detected proteins are shown on the left side of the photographs.

In FIG. 2, in the cells to which only the IgG heavy chain had been introduced (Lane 1) and the cells to which only the HLA-DR had been introduced (Lanes 2 to 4), although IgG heavy chain expression or HLA-DR expression was observed as can be seen from the first and third photographs from the top, the binding between the IgG heavy chain and the HLA-DR was not observed as can be seen from the second photograph. In contrast, in the cells to which the IgG heavy chain and the rheumatism susceptible HLA-DR4 (HLA-DRA*01:01/HLA-DRB1*04:04) had been introduced (Lane 5), IgG heavy chain expression and HLA-DR expression were observed as can be seen from the first and third photographs, and besides, the binding between the IgG heavy chain and the HLA-DR also was observed as can be seen from the second photograph. In the cells to which the IgG heavy chain and the rheumatism resistant HLA-DR3 (HLA-DRA*01:01/HLA-DRB1*03:01) had been introduced (Lane 6), although IgG heavy chain expression and HLA-DR expression were observed, the binding between the HLA-DR and the IgG heavy chain was lower than that in the cells to which the rheumatism susceptible HLA-DR4 had been introduced (Lane 5). In the cells to which the HLA-DRA*01:01/Cw3-pep-HLA-DRB1*04:04 had been introduced (Lane 7), although IgG heavy chain expression and HLA-DR expression were observed, the binding between the HLA-DR and the IgG heavy chain was much lower than that in the cells of Lane 5 (HLA-DR4), because the binding properties at the peptide-binding site were inhibited by the peptide. From these results, it was found that HLA-DR is necessary for IgG heavy chain expression on a cell surface and that an IgG heavy chain is presented on a cell surface with being bound to the peptide-binding groove of HLA-DR.

Example 1C

The present example examined whether rheumatoid factor (RF) and an RF61 rheumatoid factor antibody (RF61, mAb) recognize an IgG heavy chain presented by HLA-DR.

Polynucleotides encoding variable regions of the heavy chain and lambda light chain of an RF61 rheumatoid factor antibody were synthesized on the basis of Accession No. X54437 and Accession No. X54438, respectively. The polynucleotide encoding the heavy chain was introduced to a pME18S vector containing a polynucleotide encoding the constant region of a secretory mouse IgG1 heavy chain (Accession No. L247437.1), and the polynucleotide encoding the lambda light chain (Accession No. X06876) was introduced to a pME18S vector containing a polynucleotide encoding the constant region of a human lambda chain, both in such a manner that they were ligated functionally. Then, the heavy chain-containing vector and the light chain-containing vector were introduced to 293T cells and the 293T cells were cultured in the same manner as in Example 1A. After the culture, the culture supernatant containing the RF61 antibody was collected. The thus-obtained supernatant was used as RF61.

In the same manner as in Example 1A, the HLA-DRA*01:01 vector as an α-chain expression vector, the HLA-DRB1*04:04 vector as a β-chain expression vector, the sIgGH vector for secretory IgG heavy chain expression, and the GFP vector were introduced to 293T cells, the 293T cells were cultured, the cultured cells were reacted with the respective antibodies, and GFP-positive cells were subjected to flow cytometry analysis. Specifically, for examination of RF binding, the cells were reacted with RF-containing diluted serums of rheumatic patients, and further reacted with an APC-labeled anti-human IgM antibody. The diluted serums were obtained by diluting the patient serums 300-fold. For examination of RF61 binding, a dimer composed of the RF61 and the APC-labeled anti-mouse IgG Fc antibody was formed beforehand, and the cells were reacted with the dimer. For examination of IgG heavy chain expression or HLA-DR expression on the cell surfaces, the cells were reacted with the anti-IgG antibody or the anti-HLA-DR antibody and further with the APC-labeled anti-mouse IgG Fab antibody in the same manner as in Example 1A.

APC-labeled anti-human IgM antibody: available from Jackson ImmunoResearch, Code: 709-136-073

As Control 1, flow cytometry analysis was performed in the same manner, except that the HLA-DR expression vectors were not introduced. As Control 2, flow cytometry analysis was performed in the same manner, except that the mIgGH vector for membrane IgG heavy chain expression, the IgGL vector for IgG light chain expression, the Igα vector, and the Igβ vector were introduced, instead of the sIgGH vector for secretory IgG heavy chain expression.

Figure 3:
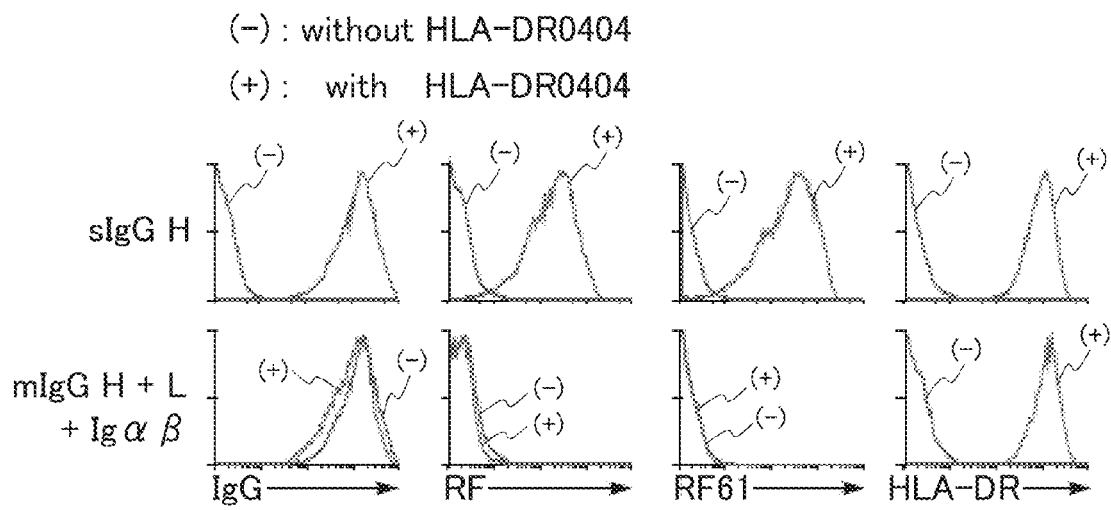
FIG. 3 shows histograms showing the expression level of IgG or MHC class II molecules on cell surfaces or the amount of binding of a rheumatoid factor or an RF61 rheumatoid factor to an IgG heavy chain presented by the MHC class II molecules in Example 1C.

The results obtained are shown in FIG. 3. FIG. 3 shows histograms showing the expression level of the IgG heavy chain or the HLA-DR on the cell surfaces, or the amount of binding of the RF or the RF61 on the cell surfaces. In FIG. 3, the horizontal axis indicates the fluorescence intensity, which shows the expression level of the IgG heavy chain presented by the HLA-DR or the expression level of the HLA-DR, or the amount of binding of the RF or the RF61, and the vertical axis indicates the cell counts. In FIG. 3, the upper row shows the results obtained regarding the cells to which the secretory IgG heavy chain had been introduced, and the lower row shows the results obtained regarding the cells to which the membrane IgG heavy chain, the IgG light chain, the Igα, and the Igβ had been introduced (Control 2).

As can be seen from the upper row in FIG. 3, in the cells (sIgGH) to which the HLA-DR and the secretory IgG heavy chain had been introduced, IgG heavy chain expression and HLA-DR expression on the cell surfaces were observed, and besides, the binding of the RF and the RF61 was observed. In contrast, as can be seen from the lower row in FIG. 3, in Control 2 (mIgGH+L+Igαβ), although IgG heavy chain expression and HLA-DR expression on the cell surfaces were observed, the binding of the RF and the RF61 was not observed. The reason for this is considered to be that RF and RF61 recognize misfolded IgG presented by HLA-DR, rather than correctly folded IgG containing heavy chains and light chains From these results, it was found that RF and RF61 recognize and strongly bind to a misfolded IgG heavy chain presented by HLA-DR rather than correctly folded IgG.

Example 1D

The present example examined whether IgM in serums derived from rheumatic patients recognizes an IgG heavy chain presented by HLA-DR.

RF(+) serum samples (n=5) were prepared by collecting serums from RF positive patients and diluting them 300-fold. RF(−) serum samples (n=5) were prepared by collecting serums from RF negative patients. The HLA-DRA*01:01 vector as an α-chain expression vector, the HLA-DRB1*04:04 vector as a β-chain expression vector, the IgGH vector for secretory IgG heavy chain expression, the IgG light chain vector, and the GFP vector were introduced to 293T cells, and the 293T cells were cultured. The cultured cells were reacted with the RF(+) samples or the RF(−) samples, and further reacted with the APC-labeled anti-human IgM antibody and then with the APC-labeled streptavidin. Thereafter, the binding of the autoantibody on the cell surfaces was measured by flow cytometry in the same manner as in Example 1C. As a control, flow cytometry analysis was performed in the same manner, except that the HLA-DR expression vectors were not introduced.

Figure 4:
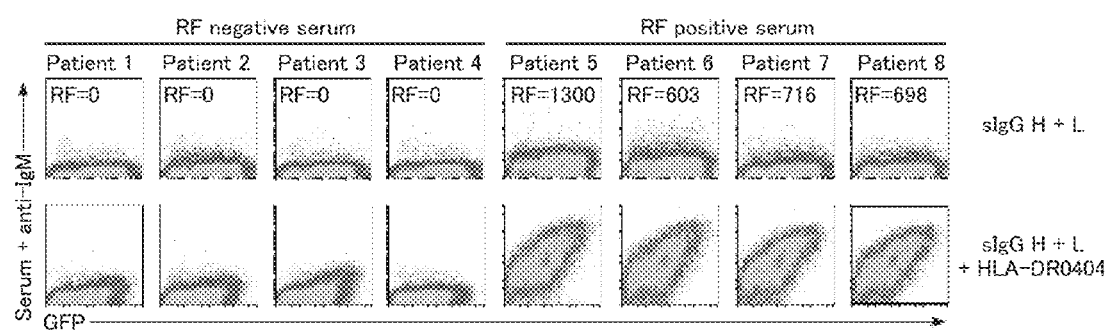
FIG. 4 shows graphs showing the amount of binding of IgM in serums derived from rheumatoid factor negative or positive patients to IgG presented by MHC class II molecules in Example 1D.

The results obtained are shown in FIG. 4. FIG. 4 shows graphs showing the expression level of GFP on the cell surfaces and the amount of binding of the autoantibody. In FIG. 4, the horizontal axis indicates the expression level of the GFP, and the vertical axis indicates the amount of binding of the RF. In FIG. 4, the upper row shows the results obtained regarding the cells without the introduction of HLA-DR (control), and the lower row shows the results obtained regarding the cells to which the HLA-DR had been introduced together with the secretory IgG heavy chain and the IgG light chain. The left four columns show the results obtained regarding the RF(−) serum samples, and the right four columns show the results obtained regarding the RF(+) serum samples.

As can be seen from the lower row in FIG. 4, in the cells (sIgGH+L+HLA-DR0404) to which the HLA-DR had been introduced together with the secretory IgG heavy chain and IgG light chain, the binding of the autoantibody was not observed when the RF(−) serum samples were used, and the binding of the autoantibody was observed when the RF(+) serum samples were used. In contrast, as can be seen from the upper row in FIG. 4, in the cells (sIgGH+L) without the introduction of HLA-DR, the binding of the autoantibody was not observed when either of the RF(+) serum samples and the RF(−) serum samples were used. The reason for this is that, in the cells (sIgGH+L) without the introduction of HLA-DR, IgG was not present on cell surfaces because: the secretory IgG was merely secreted to the outside of the cells; and without the expression of HLA-DR, IgG was not presented on the cell surfaces by HLA-DR. Thus, the IgM antibody in the serums derived from the RF positive patients did not bind to the cells to which only the secretory IgG had been introduced. From these results, it was found that an IgM antibody that binds to IgG presented by HLA class II molecules is present only in serum of RF positive patients, rather than RF negative patients.

Example 1E

The present example examined IgG heavy chain-presenting abilities of different haplotypes of HLA-DRs, and also examined whether IgM in serums derived from rheumatic patients recognizes IgG heavy chains presented by these HLA-DRs.

The HLA-DRA*01:01 vector as an α-chain expression vector, one of the HLA-DRB1*03:01 vector, the HLA-DRB1*15:01 vector, and the HLA-DRB1*04:01 vector as a β-chain expression vector, the sIgGH vector for secretory IgG heavy chain expression, and the GFP vector were introduced to 293T cells.

The cells were cultured, and thereafter, the cultured cell were subjected to flow cytometry analysis in the same manner as in Example 1C, whereby the expression levels of the IgG heavy chain and HLA-DR on the cell surfaces and the amount of binding of the autoantibody were examined. As a control, the analysis was performed in the same manner, except that the IgGH vector for secretory IgG heavy chain expression and the GFP vector were introduced to 293T cells as vectors.

Figure 5:
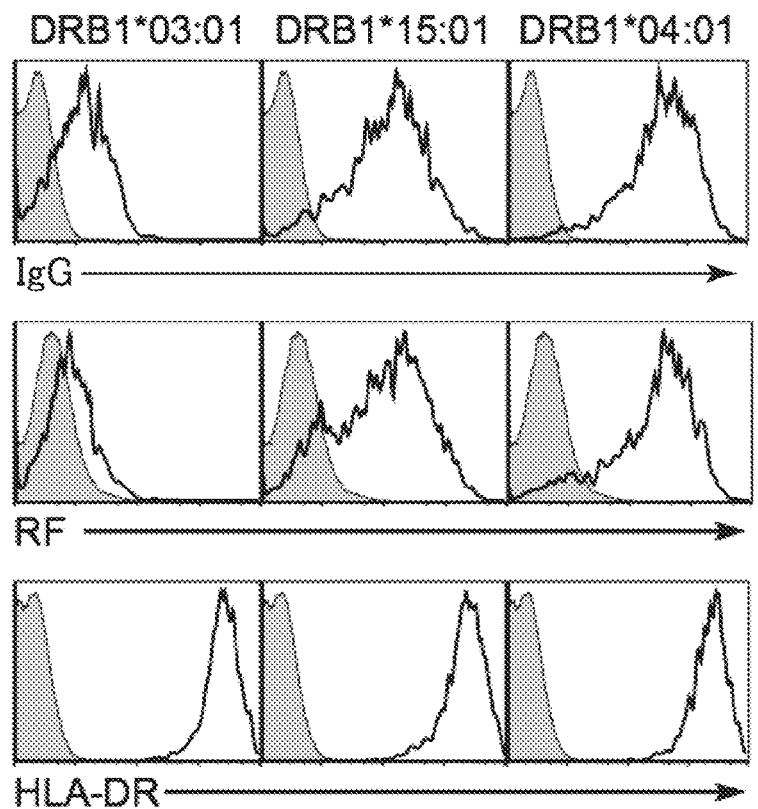
FIG. 5 shows histograms showing the expression level of an IgG heavy chain or HLA-DR on cell surfaces, or the amount of binding of an autoantibody in Example 1E.

The results obtained are shown in FIG. 5. FIG. 5 shows histograms showing the expression level of the IgG heavy chain or HLA-DR on the cell surfaces or the amount of binding of the autoantibody. In FIG. 5, the horizontal axis indicates the fluorescence intensity, which shows the expression level of the IgG presented by the HLA-DR or the expression level of the HLA-DR, or the amount of binding of the autoantibody, and the vertical axis indicates the cell counts. In FIG. 5, the left column shows the results obtained regarding the cells to which HLA-DRB1*03:01 had been introduced (HLA-DR3), the middle column shows the results obtained regarding the cells to which the HLA-DRB1*15:01 had been introduced (HLA-DR15), and the right column shows the results obtained regarding the cells to which the HLA-DRB1*04:01 had been introduced (HLA-DR4). In FIG. 5, the gray histograms show the results obtained regarding the cells to which the secretory IgG heavy chain had been introduced (control).

As can be seen from the upper row and the lower row In FIG. 5, in the cells to which the HLA-DRs with the respective haplotypes of β-chain had been introduced, IgG heavy chain expression and HLA-DR expression on the cell surfaces were observed. Also, as can be seen from the middle row, as a result of examining the expression of the IgG heavy chain presented by the HLA-DRs and the binding of RF, the binding of the autoantibody was observed in the cells to which the HLA-DRs with the respective haplotypes of β-chain had been introduced. From these results, it was found that an IgG heavy chain is presented by HLA-DR regardless of the haplotype of HLA-DR, and that an autoantibody recognizes an IgG heavy chain presented by HLA-DR regardless of the haplotype of HLA-DR.

Example 1F

The present example examined the correlation between the odds ratio for susceptibility to rheumatism and the amount of binding of an autoantibody to an autoantigen, regarding HLA-DRs with different haplotypes of β-chain.

As to the odds ratio for susceptibility to rheumatism regarding HLA-DRs with different haplotypes of β-chain, reference was made to the following literature.

Reference document: Raychaudhuri, S. et at, Five amino acids in three HLA proteins explain most of the association between MHC and seropositive rheumatoid arthritis. Nat. Genet. 44, pp. 291-296, (2012).

The HLA-DRA*01:01 vector as an α-chain expression vector, one of the respective HLA-DRB vectors shown in Table 2 as a β-chain expression vector, the sIgGH vector for secretory IgG heavy chain expression, and the GFP vector were introduced to 293T cells, and the 293T cells were cultured. Regarding the GFP-positive cultured cells, the amount of binding of the autoantibody to each of the IgG heavy chains (autoantigens) presented by HLA-DRs was measured. Specifically, flow cytometry analysis was performed on the cultured cells in the same manner as in Example 1C, and the mean fluorescent intensity of RF in the GFP-positive cells was calculated.

Then, the association between the mean fluorescent intensity and the odds ratio for susceptibility to rheumatism was analyzed using the Pearson product-moment correlation coefficient. As a control, the measurement of the mean fluorescent intensity and the analysis of the association between the mean fluorescent intensity and the odds ratio for susceptibility to rheumatism were performed in the same manner, except that the substituted HEL vector was introduced instead of the sIgGH vector for secretory IgG heavy chain expression and that an anti-Flag antibody was used.

anti-Flag antibody: Clone M2, available from Sigma

Figure 6:
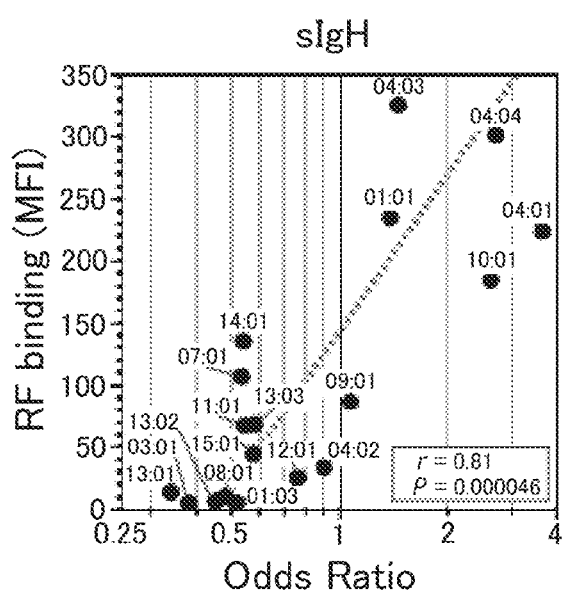
FIG. 6 is a graph showing the comparison between the amount of binding of RF to IgG presented by different haplotypes of MHC class II molecules and the odds ratio of rheumatism susceptibility in Example 1F.

The results obtained are shown in FIG. 6. FIG. 6 is a graph showing the association between the mean fluorescent intensity, which shows the amount of binding of the autoantibody, and the odds ratio for susceptibility to rheumatism. In FIG. 6, the horizontal axis indicates the odds ratio for susceptibility to rheumatism, and the vertical axis indicates the mean fluorescent intensity, which shows the amount of binding of the autoantibody. The numbers shown in FIG. 6 indicate the haplotypes of HLA-DRB (β-chain) in HLA-DRs.

As can be seen from FIG. 6, each of the different haplotypes of HLA-DRs exhibited a very high correlation ($r=0.81$, $P=0.000046$) between the amount of binding of the autoantibody to the IgG heavy chain presented by the HLA-DR and the odds ratio for susceptibility to rheumatism.

Example 1G

The present example examined whether the amount of binding of an autoantibody in serums derived from rheumatic patients to an IgG heavy chain presented by HLA-DR correlates with the RF titer.

(1) Comparison Between Amount of Binding of Autoantibody in Serums Derived from Rheumatoid Arthritis Patients and RF Titer Serum samples were prepared by collecting serums from rheumatic patients and healthy donors and diluting them 300-fold. The HLA-DRA*01:01 vector as an α-chain expression vector, the HLA-DRB1*04:04 vector as a β-chain expression vector, the IgGH vector for secretory IgG heavy chain expression, and the GFP vector were introduced to 293T cells, and the 293T cells were cultured. The cultured cells were subjected to flow cytometry analysis in the same manner as in Example 1C. The RF titer in each serum sample had been determined previously by a known ELISA method. Specifically, a human IgG Fc fragment (Jackson ImmunoResearch) was adsorbed onto a 96-microwell plate (Costar). Then, the serum sample was added to the plate to cause RF in the serum sample to bind to the human IgG Fc fragment. Further, the serum sample was reacted with a peroxidase-labeled rabbit anti-human IgM antibody (Jackson ImmunoResearch). After the reaction, the peroxidase activity was measured using a detection reagent (BD OptiEIA™, BD Bioscience). Also, using a standard serum sample with an RF titer of 1060 U/mL (GenWay Biotech, Inc.), the peroxidase activity was measured in the same manner, and the standard curve was prepared. Then, on the basis of the standard curve, the RF titer of the serum sample was calculated from the measured value of the peroxidase activity of the serum sample. As a control, the measurement was performed in the same manner, except that the serum sample was reacted only with the APC-labeled anti-human IgM antibody instead of the above-described antibody.

Figure 7:
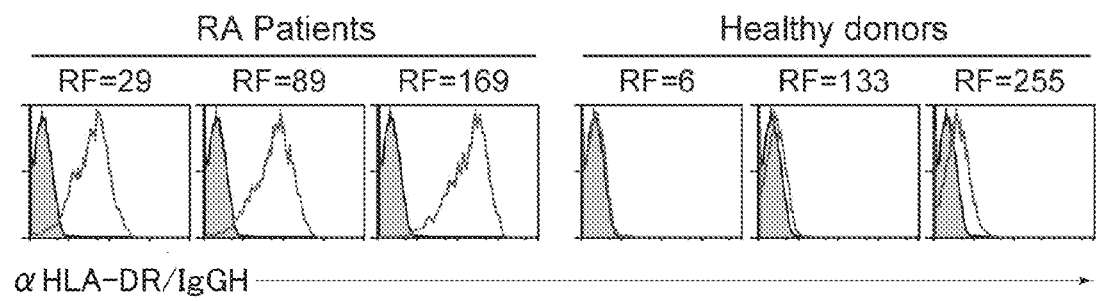
FIG. 7 shows histograms showing the amount of binding of an autoantibody on cell surfaces in Example 1G.

The results obtained are shown in FIG. 7. FIG. 7 shows histograms showing the amount of binding of the autoantibody on the cell surfaces. In FIG. 7, the horizontal axis indicates the fluorescence intensity, which shows the amount of binding of the autoantibody, and the vertical axis indicates the cell counts. Numerical values shown above the respective histograms indicate the RF titers of the respective samples. The gray histograms show the results obtained regarding the control. In FIG. 7, the left three columns show the results obtained regarding the serum samples derived from the rheumatic patients, and the right three columns show the results obtained regarding the serum samples derived from the healthy donors.

As can be seen from FIG. 7, in the control without the introduction of HLA-DR, the binding of the autoantibody was not observed. Also, as can be seen from FIG. 7, in the serum samples derived from the healthy donors, the binding of the autoantibody was not observed regardless of the RF titer. In contrast, in the serum samples derived from the rheumatic patients, the amount of binding of the autoantibody increased in proportion to the RF titer.

(2) Preparation of RF Standard Curve

The standard serum sample was diluted with a 0.1% BSA-containing HANKS buffer solution serially from 100-fold at 3.16-fold increment up to $3.16 \times 10^6$-fold. Thus, a dilution series of the standard serum sample were provided. They were used as standard samples. The RF titer of the standard serum sample was 1060 U/ml.

The mean fluorescent intensity, which shows the amount of binding of the autoantibody that recognizes an HLA-DR/IgGH complex in the standard samples to the cells, was calculated by flow cytometry analysis in the same manner as in Example 1C, except that the standard sample was used instead of the RF-containing diluted serums of the rheumatic patients. The above-described measurement of the amount of binding using the complex of HLA-DR and IgG as an antigen reagent hereinafter is referred to as "measurement by an HLA-DR/IgGH complex system", and the "anti-HLA-DR/IgGH complex antibody titer" was evaluated using this system.

Next, an RF standard curve was prepared with regard to the standard samples. Specifically, with regard to the standard samples for which the RF titers had been determined previously by the ELISA method, the measured values corresponding to their dilution factors were temporarily set to the anti-HLA-DR/IgGH complex antibody titers (aHLA-DR/IgGH, autoantibody values). Then, the RF standard curve was prepared from these temporarily set anti-HLA-DR/IgGH complex antibody titers and the mean fluorescent intensities (human IgM-MFI), which show the amounts of binding of the autoantibody that recognizes the HLA-DR4/IgGH complex, measured by the HLA-DR/IgGH complex system.

Figure 8:
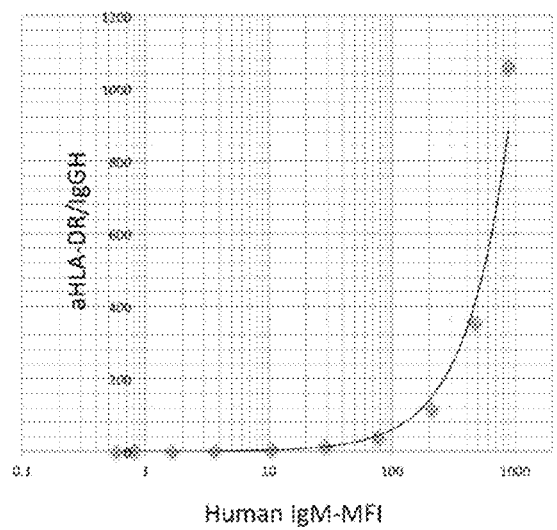
FIG. 8 is a graph showing a standard curve for an anti-HLA-DR/IgGH complex antibody titer (aHLA-DR/IgGH) in Example 1G.

The result obtained is shown in FIG. 8. FIG. 8 is a graph showing the RF standard curve. In FIG. 8, the horizontal axis indicates the mean fluorescent intensity (Human IgM-MFI), which shows the amount of binding of the autoantibody that recognizes the HLA-DR4/IgGH complex in each standard sample, measured by the HLA-DR/IgGH complex system, and the vertical axis indicates the anti-HLA-DR/IgGH complex antibody titer (aHLA-DR/IgGH) determined temporarily from the known measured value obtained by the ELISA method regarding each standard sample.

(3) Comparison Between Amounts of Binding of Autoantibodies in Serums Derived from Patients Affected with Other Diseases and RF Titer Serums derived from rheumatic patients (n=112), serums derived from systemic lupus erythematosus (SLE) patients (n=19), and serums derived from APS patients (n=117) were collected. The mean fluorescent intensity, which shows the amount of binding of the autoantibody that recognizes an HLA-DR4/IgGH complex in the serums to the cells, was calculated by flow cytometry analysis in the same manner as in the above item (2). Furthermore, on the basis of the RF standard curve shown in FIG. 8, the aHLA-DR/IgGH complex antibody value (the autoantibody value obtained by the HLA-DR/IgGH complex system) was calculated indirectly. As a control, using serums derived from healthy donors (n=127), the measurement of the amount of binding of the autoantibody that recognizes the HLA-DR4/IgGH complex and the calculation of the aHLA-DR/IgGH value (the autoantibody value obtained by the HLA-DR/IgGH complex system) based on the calibration curve were performed in the same manner. The RF titers of the serum samples had been determined previously in the same manner as in the above item (1).

Figure 9:
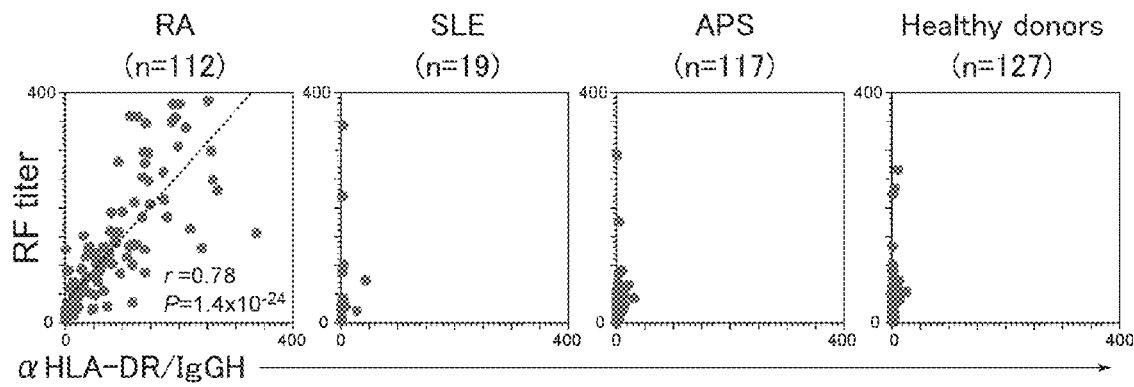
FIG. 9 shows graphs comparing the aHLA-DR/IgGH value with the RF titer in Example 1G.

The results obtained are shown in FIG. 9. FIG. 9 shows graphs comparing the aHLA-DR/IgGH value and the RF titer. In FIG. 9, the horizontal axis indicates the aHLA-DR/IgGH value, and the vertical axis indicates the RF titer. The graphs show, from the left, the results obtained regarding the serum samples derived from the rheumatic patients (RA), the serum samples derived from the SLE patients, the serum samples derived from the APS patients, and the serum samples derived from the healthy donors (Healthy donors).

As can be seen from FIG. 9, in the serum samples derived from the SLE patients, the serum samples derived from the APS patients, and the serum samples derived from the healthy donors, the binding of the autoantibody was not observed regardless of the RF titer. In contrast, in the serum samples derived from the rheumatic patients, the aHLA-DR/IgGH value increased in proportion to the RF titer. From these results, it was found that the binding of the autoantibody to the IgG heavy chain presented by HLA-DR is specific to rheumatism.

Example 2

Example 2 relates to the detection of an autoantibody as an indicator of Hashimoto's disease.

Example 2A

In the present example, HLA-DRs with different haplotypes of β-chain and thyroglobulin (TG) were expressed, and whether the TG was presented on cell surfaces by the HLA-DRs was examined.

The HLA-DRB1*01:01 vector as an α-chain expression vector, one of the HLA-DRB1*01:03 vector, the HLA-DRB1*14:03 vector, the HLA-DRB1*15:01 vector, and the HLA-DRB4*01:03 (HLA-DR53) vector as a β-chain expression vector, the TG vector, and the GFP vector were introduced to 293T cells, and the 293T cells were cultured. The cultured cells were reacted with an anti-histidine antibody, and further reacted with an APC-labeled anti-mouse IgG antibody. Thereafter, the GFP-positive cells were subjected to flow cytometry analysis in the same manner as in Example 1A. As Control 1, the analysis was performed in the same manner, except that the HLA-DR expression vectors were not introduced. Also, as Control 2, the analysis was performed in the same manner, except that only the APC-labeled anti-mouse IgG antibody was used.

anti-histidine antibody: available from Wako, Clone 9F2, monoclonal antibody (mAb)

APC-labeled anti-mouse IgG antibody: available from Jackson ImmunoResearch, Code: 715-136-150

Figure 10:
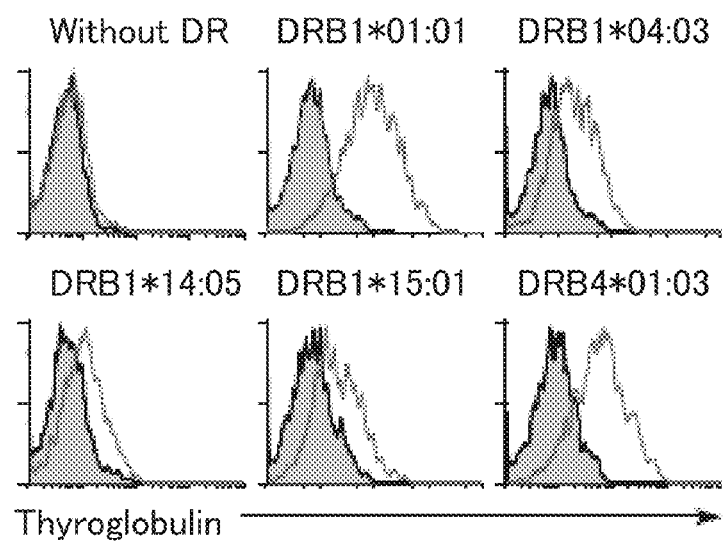
FIG. 10 shows histograms showing the expression level of thyroglobulin (TG) on cell surfaces when different haplotypes of MHC class II molecules were used in Example 2A.

The results obtained are shown in FIG. 10. FIG. 10 shows histograms showing the expression level of the TG on the cell surfaces. In FIG. 10, the horizontal axis indicates the fluorescence intensity, which shows the expression level of the TG presented by the HLA-DR, and the vertical axis indicates the cell counts. In FIG. 10, the gray histograms show the results obtained regarding Control 2.

As can be seen from FIG. 10, in the cells to which the HLA-DRs with the respective haplotypes of β-chain had been introduced, TG presented on the cell surfaces by the HLA-DRs was observed. In contrast, in Control 1 without the introduction of HLA-DR (Without DR), HLA-DR was not expressed, and the expression of TG on the cell surfaces was not observed. From these results, it was found that TG is presented by the HLA-DRs.

Example 2B

In the present example, HLA-DR was immunoprecipitated, and whether TG was bound to the HLA-DR was examined.

To 293T cells, the HLA-DRA*01:01 as an α-chain expression vector and the other respective expression vectors were introduced so as to achieve the combinations shown in FIG. 11 to be described below. The 293T cells were then cultured. The cultured cells were subjected to sample preparation by immunoprecipitation and Western blotting in the same manner as in Example 1B. In the Western blotting, TG and HLA-DR were detected using, as an antibody, an anti-human TG antibody or the rabbit anti-HLA-DR a antibody. As a control, Western blotting was performed in the same manner as in Example 1B, except that a non-immunoprecipitated sample obtained by merely lysing the cultured cells was used.

anti-human TG antibody: available from Dako

Figure 11:
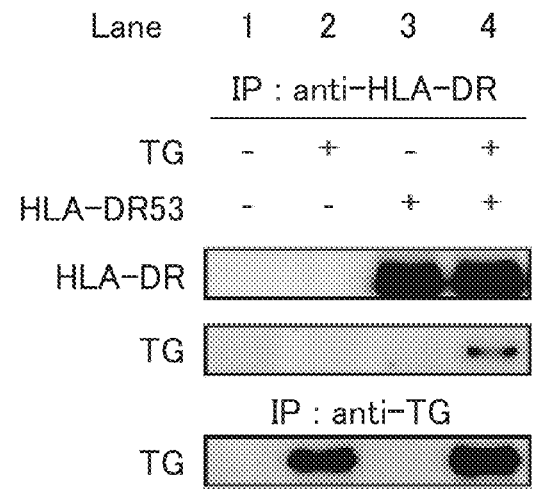
FIG. 11 shows Western blot photographs showing the binding of TG and MHC class II molecules in Example 2B.

The results obtained are shown in FIG. 11. FIG. 11 shows Western blot photographs. In FIG. 11, lane numbers and whether the expression vector had been introduced (+) or had not been introduced (−) are shown above the photographs, and the kinds of the detected proteins are shown on the left side of the photographs.

In FIG. 11, Lane 1 shows the results obtained regarding the control, and the expression was not observed. In the cells to which only the TG had been introduced (Lane 2) and the cells to which only the HLA-DR had been introduced (Lane 3), although TG expression or HLA-DR expression was observed as can be seen from the first and third photographs from the top, the binding between the TG and the HLA-DR was not observed as can be seen from the second photograph. In contrast, in the cells to which the TG and the HLA-DR had been introduced (Lane 4), TG expression and HLA-DR expression were observed as can be seen from the first and third photographs, and besides, the binding between the TG and the HLA-DR also was observed as can be seen from the second photograph. From these results, it was found that HLA-DR is necessary for TG expression on a cell surface and that TG is expressed on a cell surface with being bound to HLA-DR. Also, by immunostaining using an anti-HLA-DR antibody and an anti-TG antibody, it was found that TG is similarly presented by HLA-DR in thyroid tissues derived from Hashimoto's disease patients.

Example 2C

The present example examined whether an IgG antibody in serums derived from Hashimoto's disease patients recognizes TG presented by HLA-DR.

Serum samples were prepared by collecting serums (n=53) from anti-TG antibody positive Hashimoto's disease patients (n=3), anti-TG antibody negative Hashimoto's disease patients (n=3), and a healthy donor (n=1), and diluting them 300-fold with a 0.1% BSA-containing HANKS buffer solution. The term "anti-TG antibody" as used herein means an antibody that binds to a correctly folded TG.

The HLA-DRA*01:01 vector as an α-chain expression vector, the HLA-DRB1*01:01 (HLA-DR0101) vector or the HLA-DRB4*01:03 (HLA-DR53) vector as a β-chain expression vector, the TG vector, and the GFP vector were introduced to 293T cells, and the 293T cells were cultured. The cultured cells were reacted with each of the serum samples, and further reacted with a biotinylated anti-human IgG antibody and then with the APC-labeled streptavidin. Thereafter, regarding the GFP-positive cells, the amount of binding of the IgG antibody in the serum to the cells was measured by flow cytometry analysis in the same manner as in Example 1C. As Control 1, the measurement was performed in the same manner, except that the HLA-DR expression vectors were not introduced. As Control 2, the measurement was performed in the same manner, except that the serum sample derived from the healthy donor was used as a sample.

biotinylated anti-human IgG antibody: available from Jackson ImmunoResearch

Figure 12:
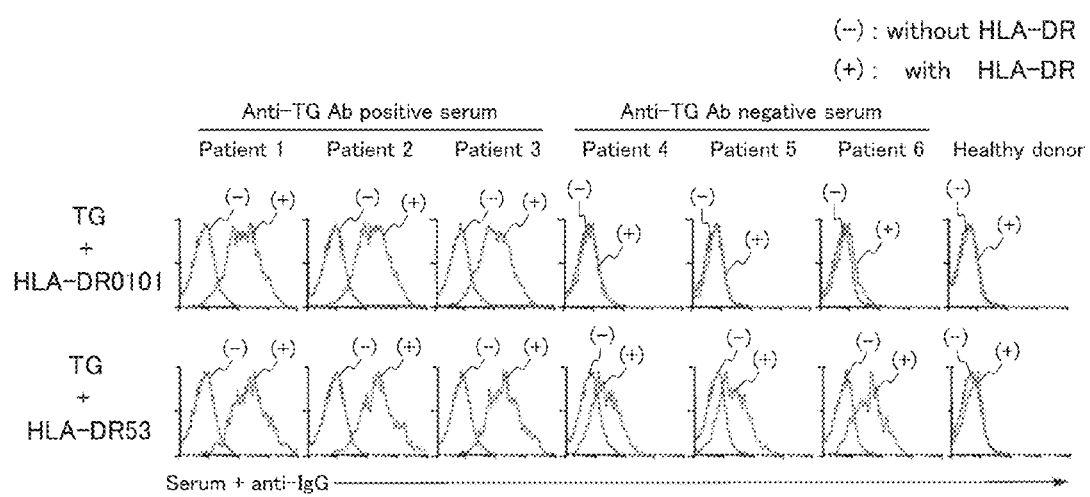
FIG. 12 shows histograms showing the amount of binding of an antibody in serums derived from anti-TG antibody negative or positive Hashimoto's disease patients or healthy donors to TG presented by different haplotypes of MHC class II molecules in Example 2C.

The results obtained are shown in FIG. 12. FIG. 12 shows histograms showing the amount of binding of the serum IgG antibody to the cells. In FIG. 12, the horizontal axis indicates the fluorescence intensity, which shows the amount of binding of the serum IgG antibody to the cells, and the vertical axis indicates the cell counts. In FIG. 12, the upper row shows the results obtained regarding the cells (TG/HLA-DR0101) to which TG and Hashimoto's disease resistant HLA-DR1 (HLA-DRA*01:01/HLA-DRB1*01:01) had been introduced, and the lower row shows the results obtained regarding the cells (TG/HLA-DR53) to which TG and Hashimoto's disease susceptible HLA-DR53 (HLA-DRA*01:01/HLA-DRB4*01:03) had been introduced. In FIG. 12, the three columns from the left (Patients 1 to 3) shows the results obtained when the anti-TG antibody positive serum samples were used, the next three columns (Patients 4 to 6) show the results obtained when the anti-TG antibody negative serum samples were used, and the one column on the right shows the result obtained when the serum sample derived from the healthy donor was used.

As can be seen from FIG. 12, when the anti-TG antibody positive serums (Patients 1 to 3) were used, the binding of the serum IgG antibody was observed in both the resistant HLA-DR cells (TG/HLA-DR1) and the susceptible HLA-DR cells (TG/HLA-DR53). In contrast, when the anti-TG antibody negative serums (Patients 4 to 6) were used, the binding of the serum IgG antibody was not observed in the resistant HLA-DR cells (TG/HLA-DR1), whereas the binding of the serum IgG antibody was observed in the susceptible HLA-DR cells (TG/HLA-DR53). From these results, it was found that, by using TG presented by susceptible HLA-DR, it is possible to detect a Hashimoto's disease patient-derived serum IgG antibody (autoantibody) that cannot be detected when a correctly folded TG is used as an antigen. Therefore, even in the case where a false negative result is obtained according to the former autoantibody detection using a correctly folded protein antigen, it is possible to detect the autoantibody, and as a result, it can be said that the risk accompanying the disease in Hashimoto's disease patients can be determined with high accuracy.

Example 2D

The present example examined whether an IgG antibody in serums derived from Hashimoto's disease patients recognizes TG presented by HLA-DR.

Serums derived from anti-TG antibody positive Hashimoto's disease patients and serum derived from anti-TG antibody negative Hashimoto's disease patients were diluted so as to achieve a predetermined dilution factor (100-, 300-, 900-, 2,700-, 8,100-, or 24,300-fold). Thus, diluted samples were prepared.

The HLA-DRA*01:01 vector as an α-chain expression vector, the HLA-DRB1*01:01 (HLA-DR0101) vector or the HLA-DRB4*01:03 (HLA-DR53) vector as a β-chain expression vector, the TG vector, and the GFP vector were introduced to 293T cells, and the 293T cells were cultured. The mean fluorescent intensity, which shows the amount of binding of the serum IgG antibody to the cells, was calculated by flow cytometry analysis in the same manner as in Example 2C, except that the cultured cells were reacted with each of the diluted samples.

Figure 13:
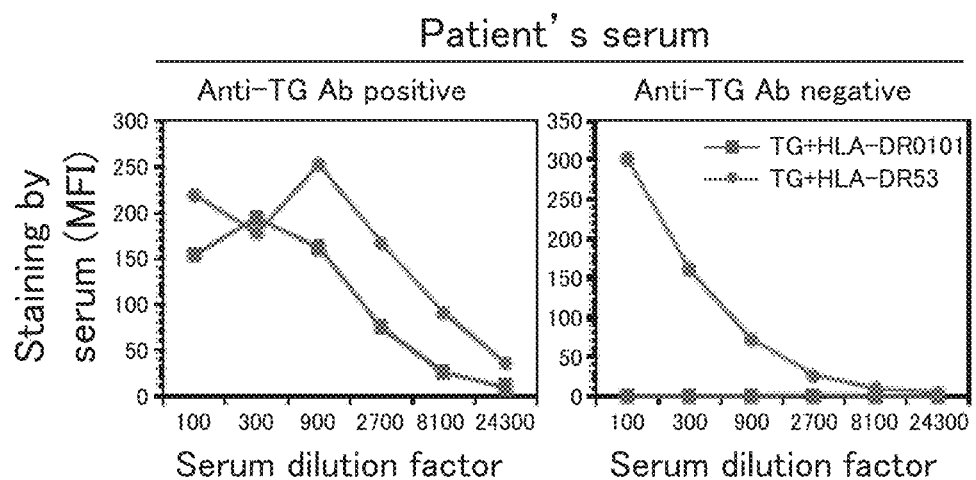
FIG. 13 shows graphs showing the amount of binding of an antibody in serially diluted serums derived from anti-TG antibody negative or positive Hashimoto's disease patients to TG presented by different haplotypes of MHC class II molecules in Example 2D.

The results obtained are shown in FIG. 13. FIG. 13 shows graphs showing the amount of binding of the serum IgG antibody to the cells (mean fluorescent intensity). In FIG. 13, the horizontal axis indicates the dilution factor of the serum, and the vertical axis indicates the mean fluorescent intensity corresponding to the amount of binding of the IgG antibody. In FIG. 13, the graph on the left shows the results obtained when the anti-TG antibody positive serum samples were used, and the graph on the right shows the results obtained when the anti-TG antibody negative serum samples were used.

In FIG. 13, as can be seen from the graph on the left, the IgG antibody in the anti-TG antibody positive serums exhibited a relatively high mean fluorescent intensity with respect to both the resistant HLA-DR cells (TG/HLA-DR1, filled square [■]) and the susceptible HLA-DR cells (TG/HLA-DR53, filled circle [●]) at a relatively low dilution factor, and the mean fluorescent intensity decreased in keeping with the increased in dilution factor of the serums. In the case of the IgG antibody in the anti-TG antibody negative serums, the mean fluorescent intensity was hardly detectable with respect to the resistant HLA-DR cells (TG/HLA-DR1, filled square [■]) at any of the dilution factors, whereas a relatively high mean fluorescent intensity was exhibited with respect to the susceptible HLA-DR cells (TG/HLA-DR53, filled circle [●]) at a relatively low dilution factor, and the mean fluorescent intensity decreased in keeping with the increased in dilution factor of the serums.

Example 2E

The present example examined whether an IgG antibody in serums derived from Hashimoto's disease patients recognizes TG presented by HLA-DR.

The mean fluorescent intensity, which shows the amount of binding of serum IgG antibody to GFP-positive cells, was calculated by flow cytometry analysis in the same manner as in Example 2D, except that serums derived from 53 Hashimoto's disease patients were diluted 300-fold in the same manner as in Example 2C and the thus-obtained diluted serums were used as serum samples.

Figure 14:
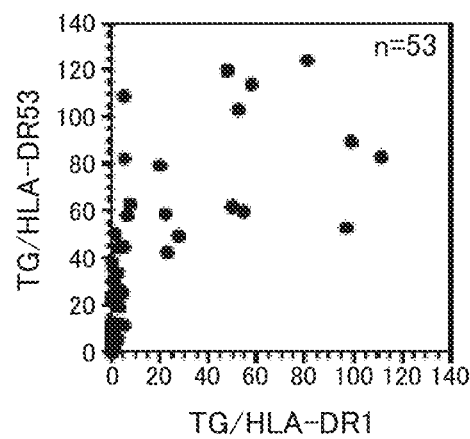
FIG. 14 is a graph comparing the amount of binding of an antibody in serums derived from Hashimoto's disease patients to TG presented by different haplotypes of MHC class II molecules in Example 2E.

The results obtained are shown in FIG. 14. FIG. 14 is a graph showing the amount of binding of the serum IgG antibody to the cells (mean fluorescent intensity). In FIG. 14, the horizontal axis indicates the amount of binding of the IgG antibody to the resistant HLA-DR cells (TG/HLA-DR1), and the vertical axis indicates the amount of binding of the IgG antibody to the susceptible HLA-DR cells (TG/HLA-DR53).

As can be seen from FIG. 14, the binding of the IgG antibody to the resistant HLA-DR cells (TG/HLA-DR1) was detected in the serums derived from some of the Hashimoto's disease patients, whereas the binding of the IgG antibody to the susceptible HLA-DR cells (TG/HLA-DR53) was detected in the serums derived from all the Hashimoto's disease patients. From these results, it was found that, by using TG presented by susceptible HLA-DR (HLA-DR53) as a detection antigen, more accurate diagnosis can be made with regard to Hashimoto's disease patients on the basis of the autoantibody detection.

Example 3

Example 3 relates to the detection of an autoantibody as an indicator of anti-phospholipid antibody syndrome (APS).

Example 3A

In the present example, HLA-DR and β2-glycoprotein I (β2-GPI) were expressed, and whether β2-GPI was presented on cell surfaces by HLA-DR and whether an anti-β2-GPI antibody and an anti-cardiolipin antibody (aCL) recognize β2-GPI presented by the HLA-DR were examined.

The HLA-DRA*01:01 vector as an α-chain expression vector, the HLA-DRB1*04:04 vector as a β-chain expression vector, the β2-GPI vector, and the GFP vector were introduced to 293T cells, and the 293T cells were cultured. The cultured cells were reacted with an anti-β2-GPI antibody or an anti-cardiolipin antibody (aCL), and further reacted with the APC-labeled anti-human IgG antibody. Then, GFP-positive cells were subjected to flow cytometry analysis in the same manner as in Example 1A. As Control 1, the analysis was performed in the same manner, except that only the β2-GPI expression vector was introduced. As Control 2, the analysis was performed in the same manner, except that only the GFP vector was introduced.

anti-β2-GPI antibody: polyclonal antibody, available from Atlas antibodies human anti-cardiolipin antibody: Clone EY2C9, supplied by Professor Atsumi, School of Medicine in Hokkaido University. Reference was made to the following paper: Ichikawa, K., M. A. Khamashta, T. Koike, E. Matsuura, and G. R. V. Hughes. 1994. P2-Glycoprotein I reactivity of monoclonal anticardiolipin antibodies from patients with the antiphospholipid syndrome. Arthritis Rheum. 37: 1453.

Figure 15:
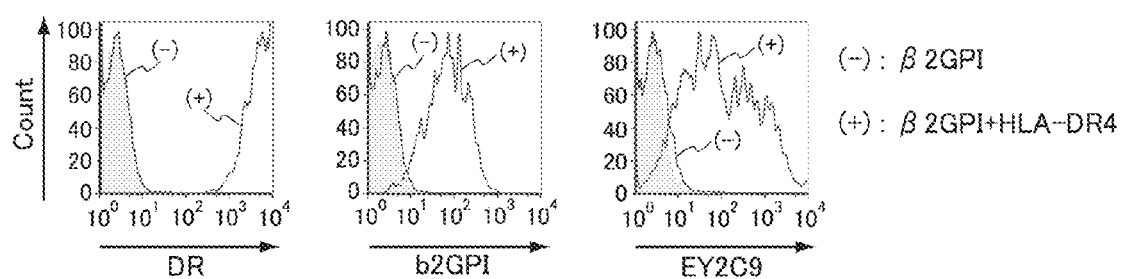
FIG. 15 shows histograms showing the expression level of β2-glycoprotein I (β2-GPI) or MHC class II molecules on cell surfaces, or the amount of binding of an anti-cardiolipin antibody to the β2-GPI presented by the MHC class II molecules in Example 3A.

The results obtained are shown in FIG. 15. FIG. 15 shows histograms showing the expression level of HLA-DR or β2-GPI on the cell surfaces or the amount of binding of the anti-cardiolipin antibody. In FIG. 15, the horizontal axis indicates the fluorescence intensity. The graph on the left shows the expression level of HLA-DR, the graph in the middle shows the expression level of β2-GPI, and the graph on the right shows the amount of binding of the anti-cardiolipin antibody. In FIG. 15, the vertical axis indicates the cell counts. In FIG. 15, the gray histograms show the results obtained regarding the cells to which only the GFP had been introduced (Control 2).

As can be seen from FIG. 15, in the cells to which HLA-DR and β2-GPI had been introduced (β2-GPI+HLA-DR4), β2-GPI presented on the cell surfaces by HLA-DR was observed, and the binding of the anti-cardiolipin antibody also was observed. In contrast, in Control 1 without the introduction of HLA-DR (β2GPI), HLA-DR was not expressed on the cell surfaces, β2-GPI expression on the cell surfaces was not observed, and the binding of the anti-cardiolipin antibody was not observed. From these results, it was found that HLA-DR is necessary for β2-GPI expression on a cell surface, and that an anti-cardiolipin antibody recognizes and binds to misfolded β2-GPI presented by HLA-DR.

Example 3B

The present example examined β2-GPI-presenting abilities of different haplotypes of HLA-DRs.

The HLA-DRA*01:01 vector as an α-chain expression vector, one of the respective HLA-DRB vectors shown in Table 2 as a β-chain expression vector, the β2-GPI vector, and the GFP vector were introduced to 293T cells.

The cells were cultured, and thereafter, the cultured cells were subjected to flow cytometry analysis in the same manner as in Example 3A, whereby the expression level of β2-GPI on the cell surfaces and the amount of binding of the anti-cardiolipin antibody were examined. Specifically, by the flow cytometry analysis, the mean fluorescent intensities of the β2-GPI and the anti-cardiolipin antibody in the GFP-positive cells were calculated. The results obtained are shown in FIGS. 16 and 17.

Figure 16:
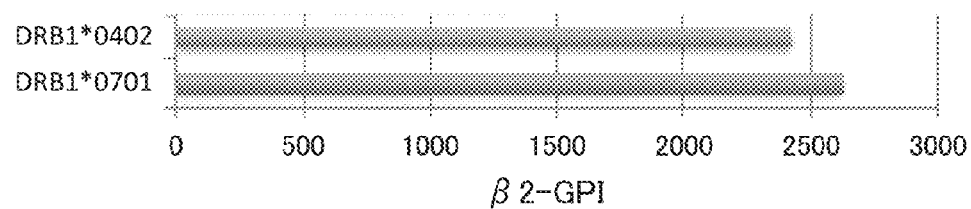
FIG. 16 is a graph showing the expression level of β2-GPI on cell surfaces when different haplotypes of MHC class II molecules were used in Example 3B.

FIG. 16 is a graph showing the expression level of the β2-GPI on the cell surfaces. In FIG. 16, the horizontal axis indicates the mean fluorescent intensity, which shows the expression level of the β2-GPI, and the vertical axis indicates the type of HLA-DRB.

As can be seen from FIG. 16, a high level of β2-GPI expression was observed when any of the HLA-DRBs was expressed. From these results, it was found that β2-GPI is presented by HLA-DR regardless of the haplotype of HLA-DR.

Figure 17:
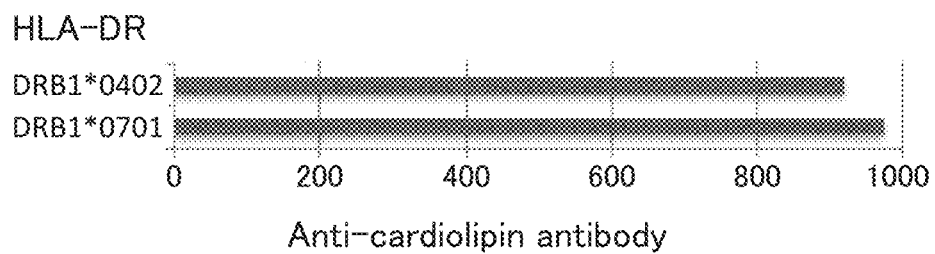
FIG. 17 is a graph showing the amount of binding of an anti-cardiolipin antibody to β2-GPI presented by the different haplotypes of MHC class II molecules in Example 3B.

Next, FIG. 17 is a graph showing the amount of binding of the anti-cardiolipin antibody. In FIG. 17, the horizontal axis indicates the mean fluorescent intensity, which indicates the amount of binding of the anti-cardiolipin antibody, and the vertical axis indicates the type of HLA-DRB.

As can be seen from FIG. 17, a large amount of binding of the anti-cardiolipin antibody was observed when any of the HLA-DRBs was expressed. From these results, it was found that the anti-cardiolipin antibody binds to β2-GPI presented by HLA-DR regardless of the haplotype of HLA-DR.

Example 3C

In the present example, HLA-DR was immunoprecipitated, and whether β2-GPI was bound to the HLA-DR was examined.

To 293T cells, the HLA-DRA*01:01 as an α-chain expression vector and the other respective expression vectors were introduced so as to achieve the combinations shown in FIG. 18 to be described below. The 293T cells were then cultured. The cultured cells were subjected to sample preparation by immunoprecipitation and Western blotting in the same manner as in Example 1B. In the immunoprecipitation, anti-HLA-DR antibody immobilized beads (biotinylated anti-HLA-DR antibody and streptavidin sepharose [GE Healthcare]) were used. In the Western blotting, β2-GPI and HLA-DR were detected using, as antibodies, either the anti-β2-GPI antibody or the rabbit anti-HLA-DRα antibody, and a peroxidase-labeled anti-rabbit IgG antibody. As Control 1, Western blotting was performed in the same manner, except that the HLA-DR vectors and the β2-GPI vector were not introduced. As Control 2, Western blotting was performed in the same manner, except that, in order to examine the expression of β2-GPI, a non-immunoprecipitated sample obtained by merely lysing the cultured cells was used.

Figure 18:
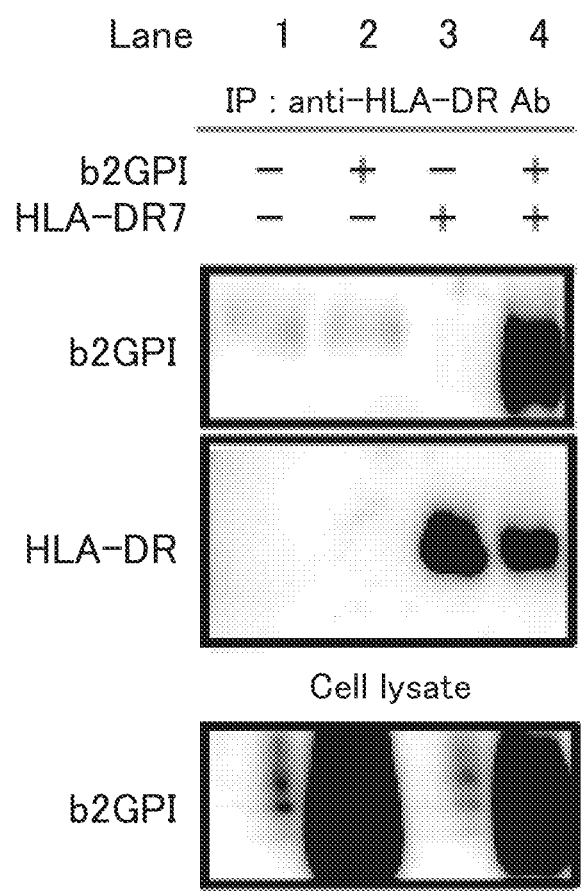
FIG. 18 shows Western blot photographs showing the binding of β2-GPI and MHC class II molecules in Example 3C.

The results obtained are shown in FIG. 18. FIG. 18 shows Western blot photographs. In FIG. 18, lane numbers and whether the expression vector had been introduced (+) or had not been introduced (−) are shown above the photographs, and the kinds of the detected proteins are shown on the left side of the photographs.

In FIG. 18, Lane 1 shows the results obtained regarding Control 1, and the expression was not observed. In the cells to which only the β2-GPI had been introduced (Lane 2) and the cells to which only the HLA-DR had been introduced (Lane 3), although β2-GPI expression or HLA-DR expression was observed as can be seen from the second and third photographs from the top, the binding between the β2-GPI and the HLA-DR was observed as can be seen from the first photograph. In contrast, in the cells to which β2-GPI and APS susceptible HLA-DR7 (HLA-DRA*01:01/HLA-DRB1*07:01) had been introduced (Lane 4), β2-GPI expression and HLA-DR expression were observed as can be seen from the second and third photographs, and besides, the binding between the β2-GPI and the HLA-DR also was observed as can be seen from the first photograph. From these results, it was found that HLA-DR is necessary for β2-GPI expression on a cell surface. Also, by immunostaining using an anti-HLA-DR antibody and an anti-β2-GPI antibody, it was found that β2-GPI is similarly presented by HLA-DR in abortive villous tissues derived from APS patients.

Example 3D

A novel measurement system that measures the autoantibody value against an HLA-DR/β2-GPI complex (aHLA-DR/β2-GPI value) without using an ELISA method was constructed. Indirect autoantibody measurement was performed with respect to serums derived from APS patients.

(1) Preparation of APS Standard Curve

Serum derived from an APS patient was diluted with a 0.1% BSA-containing HANKS buffer solution serially from 100-fold at 3.16-fold increment up to $3.16 \times 10^6$-fold. Thus, a dilution series of the serum were provided. They were used as standard samples. Regarding the serum derived from the APS patient, the measured value of anti-cardiolipin antibody (aCL) had been determined previously by a known ELISA method employing a MESACUP™ cardiolipin test and found to be 47.0 U/ml.

The HLA-DRA*01:01 vector as an α-chain expression vector, the HLA-DRB1*07:01 vector as a β-chain expression vector, the β2-GPI vector, and the GFP vector were introduced to 293T cells, and the 293T cells were cultured, in the same manner as in Example 1A. Then, the cultured cells were reacted with each of the standard samples, and further reacted with the APC-labeled anti-human IgG antibody. Thereafter, regarding the GFP-positive cells, the mean fluorescent intensity, which shows the amount of binding of the autoantibody that recognizes an HLA-DR7/β2-GPI complex in the serum to the cells, was calculated by flow cytometry analysis in the same manner as in Example 3A. The above-described measurement of the amount of binding using the complex of HLA-DR and β2-GPI as an antigen reagent hereinafter is referred to as "measurement by an HLA-DR/β2-GPI complex system", and the "anti-HLA-DR/β2-GPI complex antibody titer" was evaluated using this system.

Next, an APS standard curve was prepared with regard to the standard samples. Specifically, with regard to the standard samples for which the aCL measured values had been determined previously by the ELISA method, the measured values corresponding to their dilution factors were temporarily set to the anti-HLA-DR/β2-GPI complex antibody titers (aHLA-DR/β2-GPI, autoantibody values). Then, the APS standard curve was prepared from these temporarily set anti-HLA-DR/β2-GPI complex antibody titers and the mean fluorescent intensities (human IgG-MFI), which show the amount of binding of the autoantibody that recognizes the HLA-DR7/β2-GPI complex, measured by the HLA-DR/β2-GPI complex system.

Figure 19:
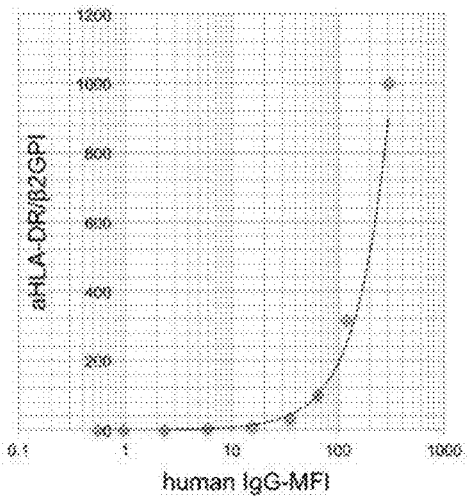
FIG. 19 is a graph showing a standard curve for an anti-HLA-DR/β2-GPI complex antibody titer (aHLA-DR/β2-GPI) in Example 3D.

The result obtained is shown in FIG. 19. FIG. 19 is a graph showing the APS standard curve. In FIG. 19, the horizontal axis indicates the mean fluorescent intensity (human IgG-MFI), which shows the amount of binding of the autoantibody that recognizes the HLA-DR7/β2-GPI complex in each standard sample, measured by the HLA-DR/GPI complex system, and the vertical axis indicates the anti-HLA-DR/β2-GPI complex antibody titer (aHLA-DR/

β2-GPI) determined temporarily from the known measured values obtained by the ELISA method regarding the standard samples.

(2) Measurement of aHLA-DR/β2-GPI Value in Serums Derived from APS Patients

Serum samples were prepared by collecting serums from APS patients (n=120) and diluting them 100-fold with a 0.1% BSA-containing HANKS buffer solution. Regarding the serums derived from the APS patients, the measured value of the anti-cardiolipin antibody (aCL) had been determined previously by the ELISA method in the same manner as in the above item (1). Also, the anti-β2-GPI antibody value (aβ2GPI) was determined by a known ELISA method.

Next, in the same manner as in the above item (1), the cultured cells were reacted with each of the serum samples, and further reacted with the APC-labeled anti-human IgG antibody. Thereafter, regarding GFP-positive cells, the mean fluorescent intensity, which shows the amount of binding of the autoantibody that recognizes an HLA-DR7/β2-GPI complex in each of the serums to the cells, was calculated by flow cytometry analysis in the same manner as in Example 3A. Furthermore, on the basis of the APS standard curve shown in FIG. 19, the aHLA-DR/β2-GPI complex antibody value (the autoantibody value obtained by the HLA-DR/GPI complex system) was calculated indirectly. As a control, using serums derived from healthy donors (n=100), the measurement of the amount of binding of the autoantibody that recognizes the HLA-DR7/β2-GPI complex and the calculation of the aHLA-DR/β2-GPI value (the autoantibody value obtained by the HLA-DR/GPI complex system) based on the calibration curve were performed in the same manner.

Figure 20:
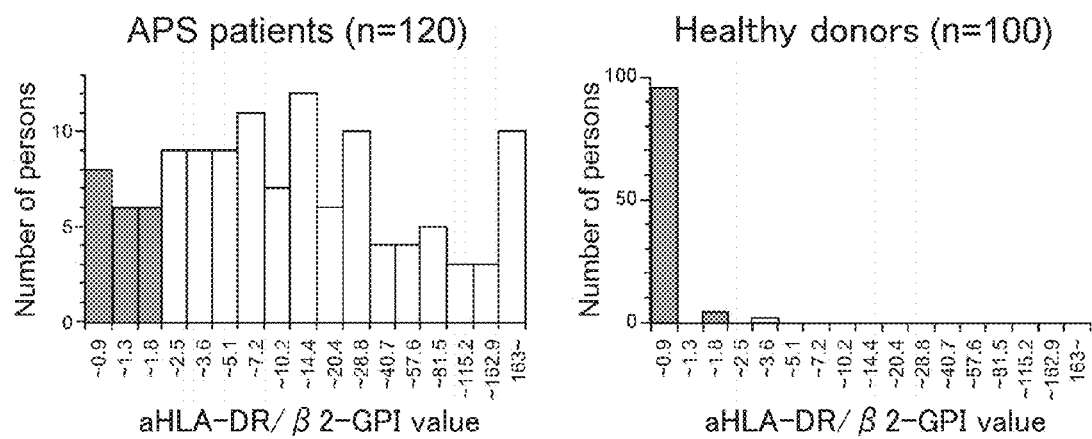
FIG. 20 shows graphs showing the anti-phospholipid antibody calculated value (aHLA-DR/β2-GPI value) obtained by an HLA-DR/β2-GPI complex system, regarding serums of anti-phospholipid antibody syndrome patients and healthy donors in Example 3D.

First, FIG. 20 shows graphs showing the distribution of the autoantibody value (aHLA-DR/β2-GPI value) obtained by the HLA-DR/GPI complex system with regard to the serum samples derived from the APS patients (n=120) and the healthy donors (n=100). In FIG. 20, the horizontal axis indicates the ranges of the autoantibody value (aHLA-DR/β2-GPI Ab), and the vertical axis indicates the number of patients falling within the respective ranges of the aHLA-DR/β2-GPI value. The reference value was set to 1.8 U/mL, which corresponds to 99 percentile of the aHLA-DR/β2-GPI value in the 100 healthy donors. In FIG. 20, the aHLA-DR/β2-GPI values in the ranges equal to or greater than the reference value are indicated with open bars, and the aHLA-DR/β2-GPI values in the ranges smaller than the reference value are indicated with gray bars. As can be seen from FIG. 20, among the 120 APS patients, 100 patients (83.3%) exhibited a value greater than the reference value (determined as APS positive). Between the APS patients and the healthy donors, a significant difference in aβ2-GPI/DR7 value was observed ($p=3.3 \times 10^{-33}$). From these results, it was found that, by using an HLA-DR/β2-GPI complex as an antigen reagent and calculating the autoantibody value indirectly using the APS standard curve according to the HLA-DR/GPI complex system, the risk of APS can be determined with high accuracy.

Figure 21A:
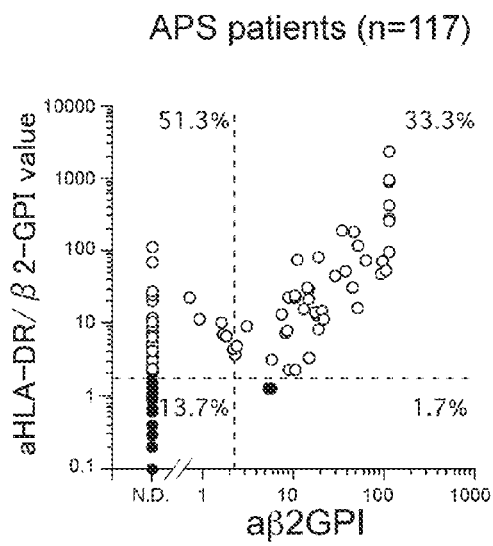
FIG. 21 shows graphs comparing, regarding serums of APS patients, the autoantibody value (aHLA-DR/β2-GPI value) obtained by the HLA-DR/β2-GPI complex system with the anti-phospholipid antibody measured value or the anti-cardiolipin antibody measured value obtained by an ELISA method in Example 3D.
Figure 21B:
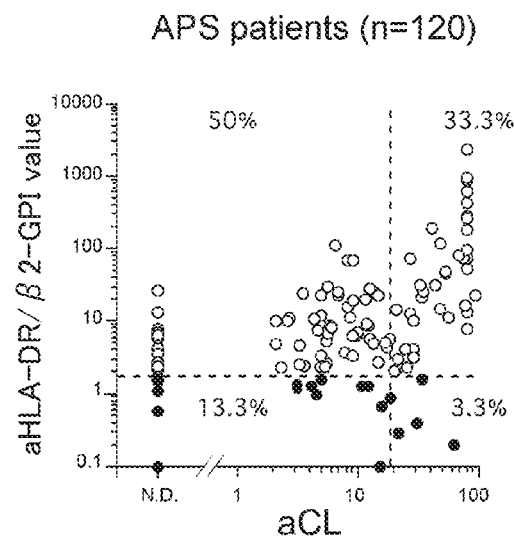

Next, FIG. 21 shows graphs comparing, regarding the serum samples derived from the APS patients, the autoantibody value (aHLA-DR/β2-GPI value) calculated by the HLA-DR/GPI complex system with the anti-β2-GPI antibody measured value (aβ2GPI) and the anti-cardiolipin antibody measured value (aCL) obtained by the ELISA method, respectively. In FIG. 21A, the horizontal axis indicates the anti-β2-GPI antibody measured value obtained by the ELISA method. In FIG. 21B, the horizontal axis indicates the anti-cardiolipin antibody measured value. In FIGS. 21A and 21B, the vertical axis indicates the autoantibody value (aHLA-DR/β2-GPI value) obtained by the HLA-DR/GPI complex system. In FIG. 21A, a dotted line extending vertically indicates the reference value (2.2 U/mL) for the anti-β2-GPI antibody measured value. In FIG. 21B, a dotted line extending vertically indicates the reference value (18.5 U/mL) for the anti-cardiolipin antibody measured value. In FIGS. 21A and 21B, a dotted line extending horizontally indicates the reference value (1.8 U/mL) for the aHLA-DR/β2-GPI value. The reference value for the anti-β2-GPI antibody measured value and the reference value for the anti-cardiolipin antibody measured value correspond to 99 percentile of the anti-β2-GPI antibody measured value and the anti-cardiolipin antibody measured value in the serum samples derived from the healthy donors, respectively. In FIGS. 21A and 21B, open circles (○) indicate the serum samples exhibiting the aHLA-DR/β2-GPI value equal to or greater than the reference value, and filled circles (●) indicate the serum samples exhibiting the aHLA-DR/β2-GPI value smaller than the reference value. In FIGS. 21A and 21B, the numbers shown in the graphs indicate the proportions of the serum samples in the respective fractions.

As can be seen from FIG. 21A, 35% of the APS patients were determined as APS positive from the anti-β2-GPI antibody measured value, whereas 84.6% of the APS patients were determined as APS positive from the autoantibody value obtained by the HLA-DR/GPI complex system. Furthermore, as can be seen from FIG. 21B, 36.6% of the APS patients were determined as APS positive from the anti-cardiolipin antibody measured value, whereas 83.3% of the APS patients were determined as APS positive from the autoantibody value obtained by the HLA-DR/GPI complex system. Still further, as can be seen from the upper left fraction in FIGS. 21A and 21B, about 80% of the APS patients determined as APS negative from the anti-β2-GPI antibody measured value or the anti-cardiolipin antibody measured value were determined as APS positive from the autoantibody value obtained by the HLA-DR/GPI complex system. From these results, it was found that, on the basis of the autoantibody value calculated using the HLA-DR/GPI complex system as an antigen reagent, APS patients can be determined as APS positive with higher accuracy as compared with the determination using the anti-β2-GPI antibody measured value or the anti-cardiolipin antibody measured value obtained by the conventional ELISA method, for example. Also, it was found that APS patients determined as APS negative by the conventional ELISA method also can be determined correctly as APS positive. Therefore, it can be said that the present invention can determine the risk of APS with higher accuracy than conventional ELISA methods using a correctly folded β2-GPI.

Example 4

Example 4 relates to the detection of an autoantibody as an indicator of Basedow's disease (Graves' disease).

The present example examined whether an autoantibody in serum derived from a Basedow's disease patient recognizes TSHR presented by HLA-DR.

Serum samples were prepared by collecting serums from Basedow's disease patients and healthy donors and diluting them 300-fold. In the same manner as in Example 1A, the HLA-DPA*02:02 vector as an α-chain expression vector, the HLA-DPB*05:01 vector as a β-chain expression vector, the TSHR vector, and the GFP vector were introduced to 293T cells, the 293T cells were cultured, the cultured cells were reacted with the respective antibodies or the serums, and flow cytometry analysis was performed on the GFP-positive cells. Specifically, in order to examine the binding of the autoantibody in the serums derived from the Basedow's disease patients, the cells were reacted with the diluted serums of the Basedow's disease patients, and further reacted with an APC-labeled anti-human IgM antibody. Furthermore, in order to examine TSHR expression or HLA-DP expression on the cell surfaces, flow cytometry analysis was performed in the same manner as in Example 1A, except that the cells were reacted with an anti-TSHR antibody or an anti-HLA-DP antibody, and further reacted with the APC-labeled anti-mouse IgG Fab antibody.

anti-human TSHR antibody: available from Santa Cruz, Clone 2C11 anti-human HLA-DP antibody: available from ExBio, Clone HL-38

As Control 1, flow cytometry analysis was performed in the same manner, except that the HLA-DP expression vectors were not introduced. As Control 2, flow cytometry analysis was performed in the same manner, except that the cells were reacted only with the APC-labeled anti-human IgM antibody or the APC-labeled anti-mouse IgG Fab antibody, instead of the above-described antibodies.

Figure 22:
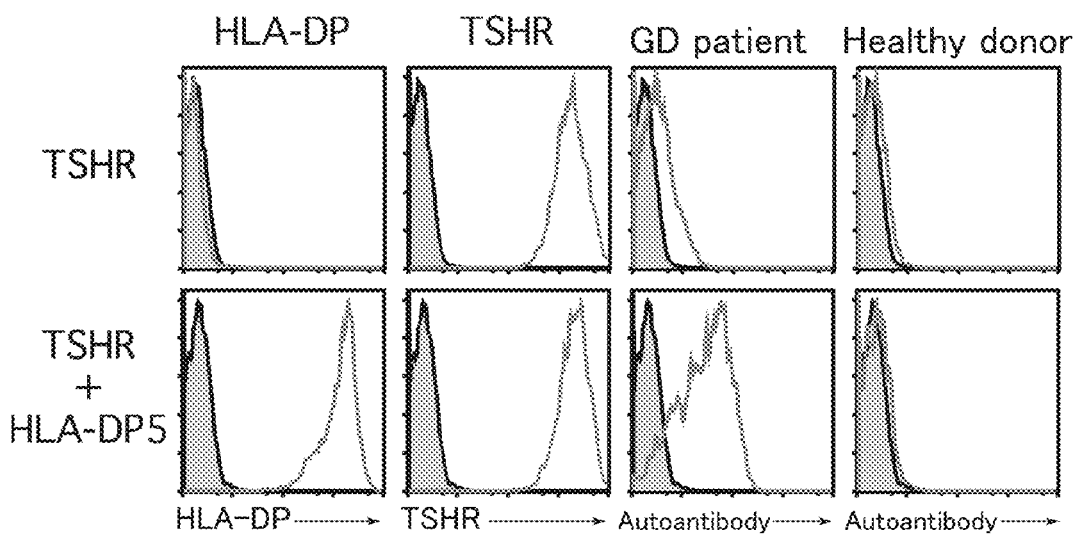
FIG. 22 shows histograms showing the expression level of TSHR or MHC class II molecules on cell surfaces or the amount of binding of an autoantibody to TSHR presented by the MHC class II molecules in Example 4.

The results obtained are shown in FIG. 22. FIG. 22 shows histograms showing the expression level of TSHR or the MHC class II molecule on the cell surfaces or the amount of binding of the autoantibody to the TSHR presented by the MHC class II molecule. In FIG. 22, the horizontal axis indicates the fluorescence intensity, which shows the expression levels of HLA-DP and TSHR or the amount of binding of the autoantibody in the serum samples, and the vertical axis indicates the cell counts. In FIG. 22, the upper row shows the results obtained regarding the cells to which TSHR had been introduced (Control 1), and the lower row shows the results obtained regarding the cells to which TSHR and the MHC class II molecule had been introduced. As can be seen from the lower row in FIG. 22, in the cells to which the HLA-DR and the TSHR had been introduced (TSHR+HLA-DP5), TSHR expression and HLA-DP expression on the cell surfaces were observed, and besides, the binding of the autoantibody in the serum samples derived from the Basedow's disease (GD) patients was observed. In contrast, as can be seen from the upper row in FIG. 22, in Control 1 (TSHR), although TSHR expression on the cell surfaces was observed, the binding of the autoantibody in the serum samples derived from the Basedow's disease patients was not observed. Furthermore, in any cell groups, the binding with an antibody in the serum samples derived from the healthy donors was not observed. From these results, it was found that an autoantibody in a serum sample derived from a Basedow's disease patient recognizes and strongly binds to a misfolded TSHR presented by HLA-DP rather than a correctly folded TSHR.

While the present invention has been described above with reference to illustrative embodiments, the present invention is by no means limited thereto. Various changes and modifications that may become apparent to those skilled in the art may be made in the configuration and specifics of the present invention without departing from the scope of the present invention.

This application claims priority from Japanese Patent Application No. 2013-148833 filed on Jul. 17, 2013. The entire disclosure of this Japanese patent application is incorporated herein by reference.

INDUSTRIAL APPLICABILITY

According to the present invention, an autoantibody involved in an autoimmune disease can be detected with high accuracy by using the denatured protein/MHC class II as an antigen reagent for detecting the autoantibody. Accordingly, the present invention can inhibit the problem of a false negative, thus allowing the possibility of an autoimmune disease to be determined with high accuracy. Therefore, the present invention is very useful in the fields of clinical practice and biochemistry, for example.

SEQUENCE LISTING

TF13042WO_2013.11.19_ST25.txt

The invention claimed is:

1. A detection method for detecting an autoantibody, the detection method comprising the steps of:
   causing a sample and an antigen reagent comprising a denatured protein presented by an MHC class II molecule to come into contact with each other; and
   detecting a complex of an autoantibody in the sample and the denatured protein in the antigen reagent,
   wherein the denatured protein is a misfolded protein resulting from denaturation of folding in a correctly folded protein.

2. The detection method according to claim 1, wherein the denatured protein is a denatured protein presented by an MHC class II molecule, obtained by introducing a gene encoding a correctly folded protein into an MHC class II molecule expression system cell.

3. The detection method according to claim 1, wherein the denatured protein is a protein resulting from denaturation of a correctly folded protein involved in an autoimmune disease.

4. The detection method according to claim 1, wherein the denatured protein is a protein resulting from denaturation of at least one selected from the group consisting of an IgG heavy chain, thyroglobulin, β2-glycoprotein I, and a thyroid-stimulating hormone receptor.

5. The detection method according to claim 1, wherein the MHC class II molecule is at least one selected from the group consisting of HLA-DR, HLA-DP, and HLA-DQ.

6. The detection method according to claim 1, wherein the MHC class II molecule is at least one selected from the group consisting of HLA-DR1, HLA-DR2, HLA-DR3, HLA-DR4, HLA-DR5, HLA-DR6, HLA-DR7, HLA-DR8, HLA-DR13, HLA-DR14, HLA-DR15, HLA-DQ3, HLA-DQ6, HLA-DQ8, HLA-DP4, and HLA-DP5.

7. The detection method according to claim 1, wherein combination of the MHC class II molecule and the denatured protein is at least one selected from the group consisting of the following combinations (1) to (4):
(1) the MHC class II molecule is HLA-DR, and the denatured protein is a denatured protein resulting from denaturation of an IgG heavy chain;
(2) the MHC class II molecule is HLA-DR, and the denatured protein is a denatured protein resulting from denaturation of thyroglobulin;
(3) the MHC class II molecule is HLA-DR, and the denatured protein is a denatured protein resulting from denaturation of β2-glycoprotein I; and
(4) the MHC class II molecule is HLA-DP, and the denatured protein is a denatured protein resulting from denaturation of a thyroid-stimulating hormone receptor.

8. A test method for testing a possibility of an autoimmune disease, wherein a sample is a biological specimen isolated from a subject, the test method comprising the steps of:
   detecting a complex of an autoantibody in the sample and a denatured protein presented by an MHC class II molecule by the detection method according to claim 1; and
   evaluating the possibility of the autoimmune disease from the result of detecting the complex in the detection step,
   wherein, in the evaluation step, a measured value of the amount of complex formation obtained in the measurement step is compared with a reference value, and it is determined that the subject has a possibility of the autoimmune disease when the measured value is higher than the reference value, and
   the reference value is the amount of complex formation in a biological specimen isolated from a healthy donor.

9. The test method according to claim 8, wherein the detection step is the step of measuring the amount of complex formation.

10. An autoantibody detection reagent for use in the detection method according to claim 1, the autoantibody detection reagent comprising:
    a denatured protein presented by an MHC class II molecule, and
    the method comprising the step of preparing an MHC class II molecule presenting a denatured protein resulting from denaturation of a correctly folded protein by introducing a gene encoding the correctly folded protein into an MHC class II molecule expression system cell.

11. A screening method for an antigen protein against an autoantibody relevant to an autoimmune disease, wherein a sample is a biological specimen isolated from a subject affected with an autoimmune disease, the screening method comprising the steps of:
    detecting a complex of an autoantibody in the sample and a denatured protein presented by an MHC class II molecule by the detection method according to claim 1; and
    determining the denatured protein that has formed the complex with the autoantibody as an antigen protein against an autoantibody relevant to the autoimmune disease.

* * * * *

```
                        SEQUENCE LISTING

<160> NUMBER OF SEQ ID NOS: 4

<210> SEQ ID NO 1
<211> LENGTH: 1581
<212> TYPE: DNA
<213> ORGANISM: Mus musculus

<400> SEQUENCE: 1
gtcttgtccc aggtcacctt gaaggagtct ggtcctgtgc tggtgaaacc cacagagacc      60
ctcacgctga cctgcagcgt ctctgggttc tcactcagca acggtagaat gggtgtgagt     120
tggatccgtc agccccagg gaaggccctg gagtgggttg gacacatttt ttcgaatgac      180
gacaaatctt acacccatc tctggagagc aggctcacca tctcccagga caccttcaga     240
agccaggtgg tcctaaccat taccaacttg gcccccgtgg acacaggcac atattattgt     300
gcacgaataa gtcgttccat ttatgggtg cttacccccg gcagcgtctg gggccaaggg     360
accatggtca ccgtctcctc agcctccacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactccac tccctcagca gcgtggtgac cgtgccctcc    600
```

-continued

| | |
|---|---|
| agcagcttgg gcacccagac ctacatctgc aacgtgaatc acaagcccag caacaccaag | 660 |
| gtggacaaga aagttgagcc caaatcttgt gacaaaactc acacatgccc accgtgccca | 720 |
| gcacctgaac tcctgggggg accgtcagtc ttcctcttcc ccccaaaacc caaggacacc | 780 |
| ctcatgatct cccggacccc tgaggtcaca tgcgtggtgg tggacgtgag ccacgaagac | 840 |
| cctgaggtca agttcaactg gtacgtggac ggcgtggagg tgcataatgc caagacaaag | 900 |
| ccgcgggagg agcagtacaa cagcacgtac cgtgtggtca gcgtcctcac cgtcctgcac | 960 |
| caggactggc tgaatggcaa ggagtacaag tgcaaggtct ccaacaaagc cctcccagcc | 1020 |
| cccatcgaga aaaccatctc caaagccaaa gggcagcccc gagaaccaca ggtgtacacc | 1080 |
| ctgcccccat cccgggatga gctgaccaag aaccaggtca gcctgacctg cctggtcaaa | 1140 |
| ggcttctatc ccagcgacat cgccgtggag tgggagagca atgggcagcc ggagaacaac | 1200 |
| tacaagacca cgcctcccgt gctggactcc gacggctcct tcttcctcta cagcaagctc | 1260 |
| accgtggaca gagcaggtg gcagcagggg aacgtcttct catgctccgt gatgcatgag | 1320 |
| gctctgcaca accactacac gcagaagagc ctctccctgt ccccggagct gcaactggag | 1380 |
| gagagctgtg cggaggcgca ggacggggag ctggacgggc tgtggacgac catcaccatc | 1440 |
| ttcatcacac tcttcctgtt aagcgtgtgc tacagtgcca ccgtcacctt cttcaaggtg | 1500 |
| aagtggatct ctcctcggt ggtggacctg aagcagacca tcatccccga ctacaggaac | 1560 |
| atgatcggac aggggggccta g | 1581 |

<210> SEQ ID NO 2
<211> LENGTH: 6
<212> TYPE: PRT
<213> ORGANISM: Artificial Sequence
<220> FEATURE:
<223> OTHER INFORMATION: sequence is synthesized

<400> SEQUENCE: 2

Gly Ser Gly Ser Gly Ser
1               5

<210> SEQ ID NO 3
<211> LENGTH: 17
<212> TYPE: PRT
<213> ORGANISM: Artificial Sequence
<220> FEATURE:
<223> OTHER INFORMATION: sequence is synthesized

<400> SEQUENCE: 3

Gly Ser His Ser Met Arg Tyr Phe Tyr Thr Ala Val Ser Arg Pro Gly
1               5                   10                  15

Arg

<210> SEQ ID NO 4
<211> LENGTH: 720
<212> TYPE: DNA
<213> ORGANISM: Aequorea victoria

<400> SEQUENCE: 4

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |

```
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```